(12) United States Patent
Haslam et al.

(10) Patent No.: US 12,277,712 B2
(45) Date of Patent: Apr. 15, 2025

(54) METHOD FOR GENERATING A 3D PHYSICAL MODEL OF A PATIENT SPECIFIC ANATOMIC FEATURE FROM 2D MEDICAL IMAGES

(71) Applicant: Axial Medical Printing Limited, Belfast (GB)

(72) Inventors: Niall Haslam, Belfast (GB); Lorenzo Trojan, Belfast (GB); Daniel Crawford, Belfast (GB)

(73) Assignee: Axial Medical Printing Limited, Belfast (GB)

( * ) Notice: Subject to any disclaimer, the term of this patent is extended or adjusted under 35 U.S.C. 154(b) by 0 days.

(21) Appl. No.: 18/595,213

(22) Filed: Mar. 4, 2024

(65) Prior Publication Data
US 2024/0202927 A1 Jun. 20, 2024

Related U.S. Application Data

(63) Continuation of application No. 18/359,821, filed on Jul. 26, 2023, now Pat. No. 11,922,631, which is a
(Continued)

(30) Foreign Application Priority Data

Oct. 14, 2016 (GB) .................................... 1617507

(51) Int. Cl.
*G06K 9/00* (2022.01)
*G06F 18/24* (2023.01)
(Continued)

(52) U.S. Cl.
CPC ................ *G06T 7/11* (2017.01); *G06F 18/24* (2023.01); *G06T 7/0014* (2013.01); *G06T 17/20* (2013.01);
(Continued)

(58) Field of Classification Search
CPC .. G06N 3/08; G06N 7/01; G06N 5/04; G06N 3/045; G06N 3/084; G06N 20/00;
(Continued)

(56) References Cited

U.S. PATENT DOCUMENTS

| 5,859,891 A | 1/1999 | Hibbard |
| 9,437,119 B1 | 9/2016 | Bernal |

(Continued)

FOREIGN PATENT DOCUMENTS

| CN | 105608728 A | 5/2016 |
| CN | 106373168 A | 2/2017 |

(Continued)

OTHER PUBLICATIONS

Richmond, Mapping Stacked Decision Forests to Deep and Sparse Convolutional Neural Networks for Semantic Segmentation, 2015, arXiv (Year: 2015).*

(Continued)

*Primary Examiner* — Alex Kok S Liew
(74) *Attorney, Agent, or Firm* — Greenberg Traurig, LLP; Christopher C. Bolten; Albert K. Heng

(57) ABSTRACT

There is provided a method for generating a 3D physical model of a patient specific anatomic feature from 2D medical images. The 2D medical images are uploaded by an end-user via a Web Application and sent to a server. The server processes the 2D medical images and automatically generates a 3D printable model of a patient specific anatomic feature from the 2D medical images using a segmentation technique. The 3D printable model is 3D printed as a 3D physical model such that it represents a 1:1 scale of the patient specific anatomic feature. The method includes the step of automatically identifying the patient specific anatomic feature.

30 Claims, 17 Drawing Sheets

Related U.S. Application Data continuation of application No. 18/150,112, filed on Jan. 4, 2023, now Pat. No. 11,715,210, which is a continuation of application No. 17/656,189, filed on Mar. 23, 2022, now Pat. No. 11,551,420, which is a continuation of application No. 17/491,183, filed on Sep. 30, 2021, now Pat. No. 11,288,865, which is a continuation of application No. 17/115,102, filed on Dec. 8, 2020, now Pat. No. 11,138,790, which is a continuation of application No. 16/341,554, filed as application No. PCT/GB2017/053125 on Oct. 16, 2017, now Pat. No. 11,497,557.

(51) Int. Cl.
    *G06T 7/00*     (2017.01)
    *G06T 7/11*     (2017.01)
    *G06T 17/20*    (2006.01)
    *G06V 10/26*    (2022.01)
    *G16H 30/40*    (2018.01)
    *G16H 50/50*    (2018.01)
    *G16H 50/70*    (2018.01)

(52) U.S. Cl.
    CPC .............. *G06V 10/26* (2022.01); *G16H 30/40* (2018.01); *G16H 50/50* (2018.01); *G16H 50/70* (2018.01); *G06T 2200/08* (2013.01); *G06T 2207/30004* (2013.01); *G06V 2201/03* (2022.01)

(58) Field of Classification Search
    CPC .......... G06N 3/04; G06N 3/043; G06N 3/088; G06N 3/126; G06N 20/10; G06N 20/20; G06N 3/048; G06N 3/02; G06N 3/044; G06N 5/02; G06N 7/02; G06N 3/047; G06N 3/082; G06N 3/004; G06N 3/006; G06N 5/01; G06N 3/0409; G06N 3/049; G06N 5/046; G06N 7/08
    See application file for complete search history.

(56) References Cited

U.S. PATENT DOCUMENTS

| | | |
|---|---|---|
| 9,646,411 B2 | 5/2017 | Lee |
| 10,032,281 B1 | 7/2018 | Ghesu et al. |
| 10,409,235 B2 | 9/2019 | Zhou et al. |
| 10,946,586 B2 | 3/2021 | Casey et al. |
| 10,981,680 B2 | 4/2021 | Colson et al. |
| 11,010,800 B2 | 5/2021 | Norman |
| 11,059,228 B2 | 7/2021 | Elber et al. |
| 11,138,790 B2 | 10/2021 | Haslam et al. |
| 11,288,865 B2 | 3/2022 | Haslam et al. |
| 11,436,801 B2 | 9/2022 | Haslam et al. |
| 11,497,557 B2 | 11/2022 | Haslam et al. |
| 11,551,420 B2 | 1/2023 | Haslam et al. |
| 11,626,212 B2 | 4/2023 | Crawford et al. |
| 11,715,210 B2 | 8/2023 | Haslam et al. |
| 11,869,670 B2 | 1/2024 | Crawford et al. |
| 11,922,631 B2 | 3/2024 | Haslam et al. |
| 12,020,375 B2 | 6/2024 | Haslam et al. |
| 2009/0316975 A1 | 12/2009 | Kunz et al. |
| 2010/0156904 A1 | 6/2010 | Hartung |
| 2011/0038516 A1 | 2/2011 | Koehler et al. |
| 2011/0218428 A1 | 9/2011 | Westmoreland et al. |
| 2012/0059252 A1 | 3/2012 | Li et al. |
| 2012/0224755 A1 | 9/2012 | Wu |
| 2013/0002646 A1 | 1/2013 | Lin et al. |
| 2014/0328529 A1 | 11/2014 | Koceski et al. |
| 2014/0361453 A1 | 12/2014 | Triantafyllou |
| 2015/0089337 A1 | 3/2015 | Grady et al. |
| 2015/0169985 A1 | 6/2015 | Burger et al. |
| 2015/0342537 A1 | 12/2015 | Taylor et al. |
| 2016/0086078 A1 | 3/2016 | Ji et al. |
| 2016/0110517 A1 | 4/2016 | Taylor |
| 2016/0300350 A1 | 10/2016 | Choi et al. |
| 2017/0007129 A1 | 1/2017 | Kaib et al. |
| 2017/0228505 A1 | 8/2017 | Allen et al. |
| 2017/0245821 A1 | 8/2017 | Itu et al. |
| 2017/0329930 A1 | 11/2017 | Fonte et al. |
| 2018/0092699 A1 | 4/2018 | Finley |
| 2018/0165867 A1 | 6/2018 | Kuhn et al. |
| 2018/0276815 A1 | 9/2018 | Xu et al. |
| 2018/0365835 A1 | 12/2018 | Yan et al. |
| 2019/0053855 A1 | 2/2019 | Siemionow et al. |
| 2019/0105009 A1 | 4/2019 | Siemionow et al. |
| 2019/0108635 A1 | 4/2019 | Hibbard et al. |
| 2019/0205606 A1 | 7/2019 | Zhou et al. |
| 2019/0251694 A1 | 8/2019 | Han et al. |
| 2019/0392942 A1 | 12/2019 | Sorenson et al. |
| 2020/0074637 A1 | 3/2020 | Wong |
| 2020/0367970 A1 | 11/2020 | Qiu et al. |
| 2020/0402647 A1 | 12/2020 | Domracheva et al. |
| 2021/0068714 A1 | 3/2021 | Crowley et al. |
| 2021/0074425 A1 | 3/2021 | Carter et al. |
| 2021/0097690 A1 | 4/2021 | Mostapha et al. |
| 2021/0110605 A1 | 4/2021 | Haslam et al. |
| 2021/0335041 A1 | 10/2021 | Haslam et al. |

FOREIGN PATENT DOCUMENTS

| | | |
|---|---|---|
| EP | 3020537 A1 | 5/2016 |
| WO | WO-2016161198 A1 | 10/2016 |
| WO | WO-2018069736 A1 | 4/2018 |
| WO | WO-2018222779 A1 | 12/2018 |
| WO | WO-2020144483 A1 | 7/2020 |

OTHER PUBLICATIONS

Tabrizi, P.R., Zoroofi, R.A., Yokota, F. et al. Acetabular cartilage segmentation in CT arthrography based on a bone-normalized probabilistic atlas. Int J CARS 10, 433-446, 2015. (Year: 2015).*

M. Pinheiro and J. L. Alves, "A New Level-Set-Based Protocol for Accurate Bone Segmentation From CT Imaging," in IEEE Access, vol. 3, pp. 1894-1906, 2015, doi: 10.1109/ACCESS.2015.2484259. (Year: 2015).*

Richmond, A novel fast Otsu digital image segmentation method, The International Arab Journal of Information Technology, vol. 13, No. 4, Jul. 2016 (Year: 2016).*

Baghaie, et al., An Optimization Method For Slice Interpolation of Medical Images, arXiv preprint arXiv:1402.0936 (Feb. 2014).

Boulton, et al., Lessons from the National Hip Fracture Database, Orthopaedics and Trauma, 30(2):123-127 (Apr. 2016).

Brown, et al., Using Machine Learning for Sequence-Level Automated MRI Protocol Selection in Neuroradiology, Journal of the American Medical Informatics Association, 25(5):568-71 (May 2018).

Carvalho, et al., Estimating 3D lumen centerlines of carotid arteries in free-hand acquisition ultrasound, International Journal of Computer Assisted Radiology and Surgery, 7(2):207-215 (Mar. 2012).

Cui, et al., Brain MRI Segmentation with Patch-Based CNN Approach, Proceedings of the 35th Chinese Control Conference, Jul. 27-29, 2016, pp. 7026-7031.

Dou, et al., 3D Deeply Supervised Network For Automated Segmentation of Volumetric Medical Images, Medical Image Analysis, 41:40-54 (Oct. 2017).

Geremia, et al., Spatial Decision Forests for MS Lesion Segmentation in Multi-Channel Magnetic Resonance Images, NeuroImage, 57(2):378-390 (Jul. 2011).

Heckelman, et al., "Design and validation of a semi-automatic bone segmentation algorithm from MRI to improve research efficiency," Scientific Reports, vol. 12:7825, https://doi.org/10.1038/s41598-022-11785-6 (2022).

International Search Report & Written Opinion dated Feb. 16, 2018 in Int'l PCT Patent Appl. Serial No. PCT/GB2017/053125 (0110).

International Search Report & Written Opinion dated May 12, 2022 in Int'l PCT Patent Appl. Serial No. PCT/IB2022/051216 (0310).

(56) References Cited

OTHER PUBLICATIONS

International Search Report & Written Opinion dated Jun. 25, 2020 in Int'l PCT Patent Appl. Serial No. PCT/GB2020/050063 (0210).

Laosai et al., Acute Leukemia Classification by Using SVM and K-Means Clustering, 2014 Proceedings of the International Electrical Engineering Congress (IEECON), pp. 1-4 (Mar. 19, 2014).

Lee, et al., Human Airway Measurement from CT Images. In Medical Imaging 2008: Computer-Aided Diagnosis, Proc. SPIE 6915:386-383 (Mar. 2008).

Litjens, et al., A Survey on Deep Learning in Medical Image Analysis, Medical Image Analysis, 42:60-88 (Dec. 2017).

Milletari, et al., V-Net: Fully Convolutional Neural networks For Volumetric Medical Image Segmentation, arXiv preprint arXiv:1606.04797 (Jun. 2016).

Monteiro et al., "Conditional Random Fields as Recurrent Neural Networks for 3D Medical Imaging Segmentation," arXiv preprint arXiv:1807.07464, (Jul. 2019).

Mortensen et al., "Semantic Segmentation of Mixed Crops Using Deep Convolutional Neural Network," ClGr-AgEng Conference, pp. 26-29, (Jun. 2016).

Rogowska, et al., Overview and Fundamentals of Medical Image Segmentation, Handbook of Medical Imaging, Processing and Analysis, pp. 69-85 (Oct. 2000).

Schmauss D., et al., "Three-Dimensional Printing in Cardiac Surgery and Interventional Cardiology: A Single-Centre Experience," European Journal of Cardio-Thoracic Surgery, Aug. 26, 2014, vol. 47(6), pp. 1044-1052.

Yu, et al., 3D FractalNet: Dense Volumetric Segmentation for Cardiovascular MRI Volumes, In Reconstruction, Segmentation, and Analysis of Medical Images, pp. 103-110 (Oct. 2016).

Yu, et al., 3D FractaNet: dense volumetric segmentation for cardiovascular MRI Volumes. In Reconstruction, Segmentation, and Analysis of Medical Images. First International Workshops, RAMBO 2016 and HVSMR 2016. Held in Conjunction with MICCAI 2016, Athens, Greece, Oct. 17, 2016, Revised Select.

Zhou, et al., Deep convolutional neural network for segmentation of knee joint anatomy, Mag. Reson. Med., 80(6):2759-2770 (Dec. 2018).

Zhuang, J., "Laddernet: Multi-Path Networks based on U-Net For Medical Image Segmentation," arXiv:preprint arXiv:1810.07810., pp. 1-4, (Oct. 2018).

* cited by examiner

METHOD FOR GENERATING A 3D PHYSICAL MODEL OF A PATIENT SPECIFIC ANATOMIC FEATURE FROM 2D MEDICAL IMAGES

CROSS-REFERENCE TO RELATED APPLICATIONS

This application is a continuation of U.S. application Ser. No. 18/359,821, filed Jul. 26, 2023, now U.S. Pat. No. 11,922,631, which is a continuation of U.S. application Ser. No. 18/150,112, filed Jan. 4, 2023, now U.S. Pat. No. 11,715,210, which is a continuation of U.S. application Ser. No. 17/656,189, filed Mar. 23, 2022, now U.S. Pat. No. 11,551,420, which is a continuation of U.S. application Ser. No. 17/491,183, filed on Sep. 30, 2021, now U.S. Pat. No. 11,288,865, which is a continuation of U.S. application Ser. No. 17/115,102, filed on Dec. 8, 2020, now U.S. Pat. No. 11,138,790, which is a continuation of U.S. application Ser. No. 16/341,554, filed on Apr. 12, 2019, now U.S. Pat. No. 11,497,557, which claims the priority of PCT/GB2017/053125, filed on Oct. 16, 2017, which claims priority to United Kingdom Application No. GB 1617507.7, filed on Oct. 14, 2016, the entire contents of each of which are incorporated herein by reference.

BACKGROUND OF THE INVENTION

1. Field of the Invention

The field of the invention relates to a method for 3D printing a patient specific anatomic feature based on 2D medical images. More particularly, but not exclusively, it relates to methods and systems for managing the process of printing 3D physical models of specific anatomic features, methods and systems for automatically segmenting 2D medical images, and methods and systems for automatically identifying patient specific anatomic feature from 2D medical images.

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

2. Description of the Prior Art

Orthopaedic surgeons currently use traditional 2D radiological imaging (such as CT or MRI) to plan patient specific surgeries, which usually involve a clinician assessing a large number of 2D radiological images and planning operations based around their interpretations of the patient's injuries.

In 2013, £129.5 million was paid out in litigation costs as a result of complications within orthopaedic surgeries in the NHS. The orthopaedic expenditure in the NHS was approximately £10 Billion in 2016. This represents the third largest expenditure within the NHS, being just outweighed by cardiac and mental health costs. With patients typically having longer durations of life and with the increasing issue of obesity within the UK there will be an ever-expanding amount of patients requiring orthopaedic treatment and backed up by the rise of consultants within orthopaedics rising by ~250 in the past 3 years.

3D printing is receiving a great deal of attention, and may be used to create custom medical prototypes, such as patient specific implant devices. 3D printing of anatomical models from medical data was traditionally based on manual techniques associated with collecting data and prescriptive information from surgeons. The current available platforms available for processing medical data and creating 3D printed models are often very technical and require experienced users with extensive knowledge on the segmentation techniques used. In addition, segmentation techniques are also time consuming and are not automatic.

Hence current approaches do not cater to the entire medical market, as the majority of surgeons are not willing to allocate the software and training resources required to process the medical images for each applicable case.

There is a need for an easy to use and intuitive system that would leverage the advances in 3D printing and 3D visualization. It would improve the effectiveness of the surgeons' preoperative planning by producing a 3D printed model of a particular patient's injured anatomy in the required timeframe whilst maintaining the highest quality. Such a system would, in turn, further reduce costs to the healthcare provider by diminishing the chances of patient complications.

SUMMARY OF THE INVENTION

One aspect of the invention is a method for generating a 3D physical model of a patient specific anatomic feature from 2D medical images, in which: the 2D medical images are uploaded by an end-user via a Web Application and sent to a server; the server processes the 2D medical images and automatically generates a 3D printable, model of a patient specific anatomic feature from the 2D medical images using a segmentation technique; and the 3D printable model is 3D printed as a 3D physical model such that it represents a 1:1 scale of the patient specific anatomic feature.

The 2D medical images may be uploaded alongside metadata, wherein the metadata is either uploaded or entered by the end-user.

The patient specific anatomic feature may automatically be identified from analysing the 2D medical images.

The analysis of the 2D medical images may use machine learning applied to an anatomical knowledge dataset.

The patient specific anatomic feature may automatically be identified from an analysis of the metadata.

The analysis of the metadata may be done using Natural Language Processing (NLP).

The metadata may include patient's prescription information, medical professional information or any other patient-related additional information.

The metadata may be added by the end-user in real time via the Web Application.

The 3D printable model may automatically be displayed to the end-user via the Web Application, and the end-user is able review, annotate and/or modify the 3D printable model in real time.

The 2D medical images may be images from the patient taken from a CT, MRI, PET and/or SPCET scanner.

The 2D medical images and any additional metadata may be anonymised prior to being sent to the server such that no identifiable healthcare or personal information is being transferred to the server.

A cryptographic hash of the patient information may be created to enable identification of a specific patient without sharing sensitive patient information.

A smart contract object, may be required to order or initiate the generation of the 3D physical model, contains information about the requirements of the 3D physical model to be printed including one or more of: stage quality gates, insurance status, payment status/limits, clinician, patient consent, annotations, data sharing agreements and/or data processing agreements.

The smart contract object may be incorporated into a Blockchain.

The smart contract object may be pre-agreed between the patient and the end-user.

The printing of the 3D physical model may only be executed once the smart contract object has been validated.

Digital signatures may be used to verify identity and approve decisions.

Dynamic pricing may be generated after the validation of the smart contract object, and an instant quotation is displayed to the end-user.

A digital currency may be linked to the printing of the 3D physical model.

The material used for printing may be automatically selected depending on its resemblance to the specific anatomic feature.

The material used for printing may be automatically selected based on the requirement of the 3D physical model, such as the time required to achieve the printing of the 3D physical model.

The texture used for printing may be automatically selected depending on the specific anatomic feature.

The 3D physical model may be optimized based on the following patient related parameters: scan type, bone type, tissue type, age, gender, weight.

Patient related parameters may be extracted from data uploaded or entered via the Web Application.

Multiple 3D printable models may be generated and multiple 3D physical models are printed and combined when a single printer cannot print the patient anatomic feature.

One or more connective pieces may be printed in order for the multiple 3D physical models to be combined together, and the material used for printing the connective pieces is automatically predicted.

The end user may select the specific anatomic feature they wish to 3D print.

The segmentation technique may be one or a combination of the following techniques: threshold-based, decision tree, chained decision forest or neural network method.

Multiple segmentation techniques may be used, and the results of each segmentation technique are combined together to derive a final segmentation result.

A threshold-based segmentation method may be used and the threshold value is generated from the 2D medical images histogram analysis.

A threshold-based segmentation method may be used and the threshold value is a function of the type of 2D medical images (CT, MRI, PET or SPCET).

The segmentation technique may use a logistic or probabilistic function to calculate the likelihood of a pixel of being the tissue corresponding to the patient specific anatomic feature.

A threshold-based segmentation method may be used in combination with a pre-processing filter such as a Gaussian filter.

A threshold-based segmentation method may be used and the threshold value is a function of the 2D medical images scanning parameters such as X-Ray energy and/or flux.

A threshold-based segmentation method may be used and the threshold value is a function of the bone type (hard or soft).

A threshold-based segmentation method may be used and the threshold value is optimised based on one or more of the following parameters: scan type, bone type, tissue type, age, gender and weight of the patient.

A threshold-based segmentation method may be used and the threshold value is generated from the 2D medical images histogram analysis.

A threshold-based segmentation method may be used and the threshold value is generated from detecting the peaks of the 2D medical images histogram corresponding to tissues similar to the tissue of the patient specific anatomic feature.

The segmentation technique may further comprise the following steps: the detected peak inflection point is derived by calculating the zero of the histogram second derivative in proximity of each peak; the offset between a peak and the inflection point is derived; the estimated threshold corresponds to the position of the peak with an offset corresponding to three time the inflection offset.

A threshold-based segmentation method may be used and the threshold value is automatically generated and not selected by the end-user.

A threshold-based segmentation may be used and multiple thresholds are applied to the 2D medical images such that multiple 3D printable models are automatically generated.

The segmentation technique may use a decision tree, in which the following properties of the 2D medical images pixels are selected in order to create the decision tree: number of pixels resembling the tissue of interest located near the pixel in question, number of pixels resembling the tissue of interest located near the pixel in question, how strong is the overall gradient of the image at the given pixel if the consistency of the gradient direction within a small neighbourhood of the pixel, and in which the tissue of interest is the tissue corresponding to the patient specific anatomic feature.

The segmentation technique may use a decision tree, in which the decision tree is trained using existing pre-labelled medical images.

The decision tree may be applied to a subset of pixel within the original 2D medical images and the labels obtained from this subset are then up scaled using standard interpolation methods in order to recover the segmentation of the full image.

The subset of pixel may be generated by subsampling the original 2D medical images, and in which the subsampling stride is selected depending on the pixel size.

The segmentation technique may use a chained decision forest.

A hierarchy of decision forests may be used, in which the results of a decision tree and the results from another segmentation technique are fed to a new decision tree alongside the original pixel values.

Each forest-node may be treated as a simple classifier that produces a score as to how likely a pixel is to belong to the tissue corresponding to the specific patient anatomic feature.

The segmentation technique may use a Neural Network method, in which the Neural Network is trained from a database of existing medical images.

The neural network may use a Fully Convolutional Neural Network (FCNN).

The neural network may be a UNET Neural Network.

The Neural Network may include only convolutional, downsampling and upsampling layers.

The Neural Network may not include any fully connected layer and combines the ideas of uNET and FCNN in order to obtain an optimised segmentation in terms of anatomical fidelity regarding the edge of the anatomic feature.

Upsampling layers may be added and in which the outputs of previous layers are used to identify regions of the 2D medical images in order to lead to a specific classification.

The training of the Neural Network may be performed by using a database of existing medical images that have been labelled and a medical imaging ontology.

The segmentation of the 2D medical images may be performed to classify each pixel within the 2D medical images.

The segmentation step may be combined with an anatomic feature identification algorithm.

The anatomic feature identification algorithm may use a graph database of medical images anatomic features.

The method further may include establishing links between the different classified pixels from the exploration of the graph database, and identifying the patient specific anatomic feature from the established links.

The graph database may comprise nodes representing anatomic features such as tissue type and/or organ type, and edges associated with the relationships between the nodes, such as: has part, proximity, attachment, ligament, functional.

A node may include: a reference to a medical image with the corresponding anatomic feature, a reference to the results of the segmentation of a medical image with the corresponding anatomic feature, information relating to the anatomic feature such as volume, surface area, Hounsfield Unit standard deviation or average.

The graph database may be updated after the generation of a 3D printable model.

A score or probability that the anatomic feature has been correctly identified may be provided.

The method may further include a feature extraction algorithm that takes advantage of both the segmentation as well as the as the 2D medical images data in order to obtain interesting properties of the tissue or organ corresponding to the patient specific anatomic feature.

The feature extraction algorithm may be used to extract one or more of the following: the anatomic feature volume, the anatomic feature surface area, the anatomic feature Hounsfield unit, the anatomic feature standard deviation across the all available scans, histogram of the Hounsfield Units corresponding to the anatomic feature across an anatomical knowledge dataset or the smallest bounding box containing the anatomic feature.

The feature extraction algorithm may be used to extract one or more of the following: the presence of specific keypoint landmarks, a number of predefined shapes and volumes within the anatomic feature being considered or specific features that are unique to the specific anatomical component are detected.

The extracted interesting features may be added to the graph database as part of the node properties.

The extracted interesting features maybe used in order to derive a classification of the anatomical components located within the scan, using the following steps: derive accurate segmentation using one or more automated segmentation techniques; apply the feature extraction algorithm(s) to the segmentation in order to derive the values of such features; compare to the existing dataset of interesting features and attempt to find a number of matches; the matches are constrained and filtered depending on the proximity map derived from the graph database; the standard models are used to further refine the filtering and cross-checking by fitting a linear transform between the semi-classified segmented objects and what the standard model looks like; due to the inherit inaccuracies of the segmentation step, each refinement of the matches produce a score or probability of having matched the anatomical features correctly; the set of scores obtained can be used in a decision tree (or forest) in order to derive the final classification for a specific tissue or organ;

A any deviation from standard dataset may be detected.

Touching organs or tissues may be detected within the 2D medical images and an edge finding algorithm is used to separate the different tissues or organs.

The anatomic feature classification may be re-estimated once the different tissues or organs are separated.

Deformities and/or pathology of the anatomic feature may be detected by measuring the deviation from the normal or healthy appearance of the anatomic feature.

The method may be used for generating a 3D biocompatible physical model of a patient specific anatomic feature or a portion of a patient specific anatomic feature, in which the automatically segmented data is assessed against statistical model of pre-segmented anatomy 'Best fit model', and a 3D printable model is created based on a statistical model for patients' anatomy to insure an optimal reconstruction of tissue, and in which missing fragments are predetermined with a best fit model and tissue scaffold models created from this.

A 3D surface mesh model of the patient specific anatomic feature may be generated from the segmented 2D medical images.

The 3D surface mesh may be extracted from the scalar volume data.

The 3D surface mesh model may be processed by a mesh cleaning algorithm.

The 3D surface mesh model may be compressed, smoothed and reduced before being sent back to the end-user via the Web-Application.

The 3D surface mesh model may be 3D printable and has the following properties: all disjointed surfaces are closed manifolds; appropriate supports are used to keep the disjointed surfaces/volumes in place, appropriate supports are used in order to facilitate 3D printing; all surface volumes are not be hollow; if a hollow volume is specifically requested by an end-user: appropriate drainage holes are added manually by an operation team.

A 3D model of the surface of the patient specific anatomic feature may be extracted from the 3D mesh model, and in which a marching cube algorithm is used in order to force some vertices to be placed on voxels that do not intersect the iso-surface directly.

The mesh may be as close to a printable model as possible.

The method further may include a surface conditioning step.

The surface conditioning step may include the following step: poly-reduction algorithms are applied to the 3D mesh, errors such as duplicated points, overlapping surfaces, missing surface are corrected to ensure the mesh is a manifold; a mesh filter is applied; holes are detected and covered; appropriate textures are selected.

The method may further include the following steps: watertight surfaces are filled; dowels are added to support the printing of a specific anatomic feature; print supports are added by determining all local minima of the surface; the print supports are removed during printing post processing.

The generation of the 3D printable model may be performed by parallel processing.

One or more 3D printable models may be sent to the end-user via the Web-application.

The end-user may select a 3D printable model he wishes to print.

The method may be configured to detect an anomaly within the 2D medical images, such as: incorrect classification of medical images, incorrect patient data, presence of foreign objects in medical images or low quality imaging data.

An end-user may be alerted when an anomaly is detected.

The method may be able to handle 2D medical images which include unwanted artefacts or background noise, such as foreign objects or a bed.

A preview of the 3D printable model may be displayed to the end-user for approval before printing the 3D physical model.

Information on the expected timeframe to generate a 3D physical model may be calculated and displayed to the end-user in real time.

The information on the expected timeframe may take into consideration the segmentation, surface conditioning and printing phases.

The printing of a 3D physical model may be scheduled based on inbound models and surgical requirement.

The method may select a printer based on the printer parameter and the 3D physical model parameter including one or more of: build volume, materials available, minimum feature size, hollow structures within the model.

The 2D medical images and any additional metadata may be hard linked to the 3D physical model via a QR code, NFC chip or RFID tag.

The profile of an end-user may be saved alongside the end-user preference.

One or more end-users may be able to access the Web application, and in which each end-user have their own user preferences and user permissions levels.

An audit trail of the 3D printing process may be created and continuously updated and tracked.

Another aspect is a 3D printable model or file of a patient specific anatomic feature that is generated from any of the above methods.

Another aspect is a 3D physical model representing a 1:1 scale of a patient specific anatomic feature that is generated from any of the above methods.

Another aspect is a computer implemented system for generating a 3D printed model of a patient specific anatomic feature from 2D medical images, the system comprising: an interface module configured to receive 2D medical images and to send the 2D medical images to a server, a server configured to process the 2D medical images and automatically generate a 3D printable model of a patient specific anatomic feature from the 2D medical images using a segmentation technique; and a 3D printer configured to receive the 3D printable model and to 3D print a 3D physical model such that it represents a 1:1 scale of the patient specific anatomic feature.

BRIEF DESCRIPTION OF THE FIGURES

Aspects of the invention will now be described, by way of example(s), with reference to the following Figures, which each show features of the invention.

DETAILED DESCRIPTION

This Detailed Description section describes one implementation of the invention, called the Axial3D system.

The Axial3D system provides three-dimensional (3D) printed models for use in medicine, manufactured using patient data medical images to create custom products for use in a wide variety of medical applications. More specifically, the Axial3D system provides software and services that facilitates the production of bespoke 3D printed anatomical models for use by medical professionals using medical images as an input, hence bridging the gap between 3D printing technology and medicine.

Figure 1:
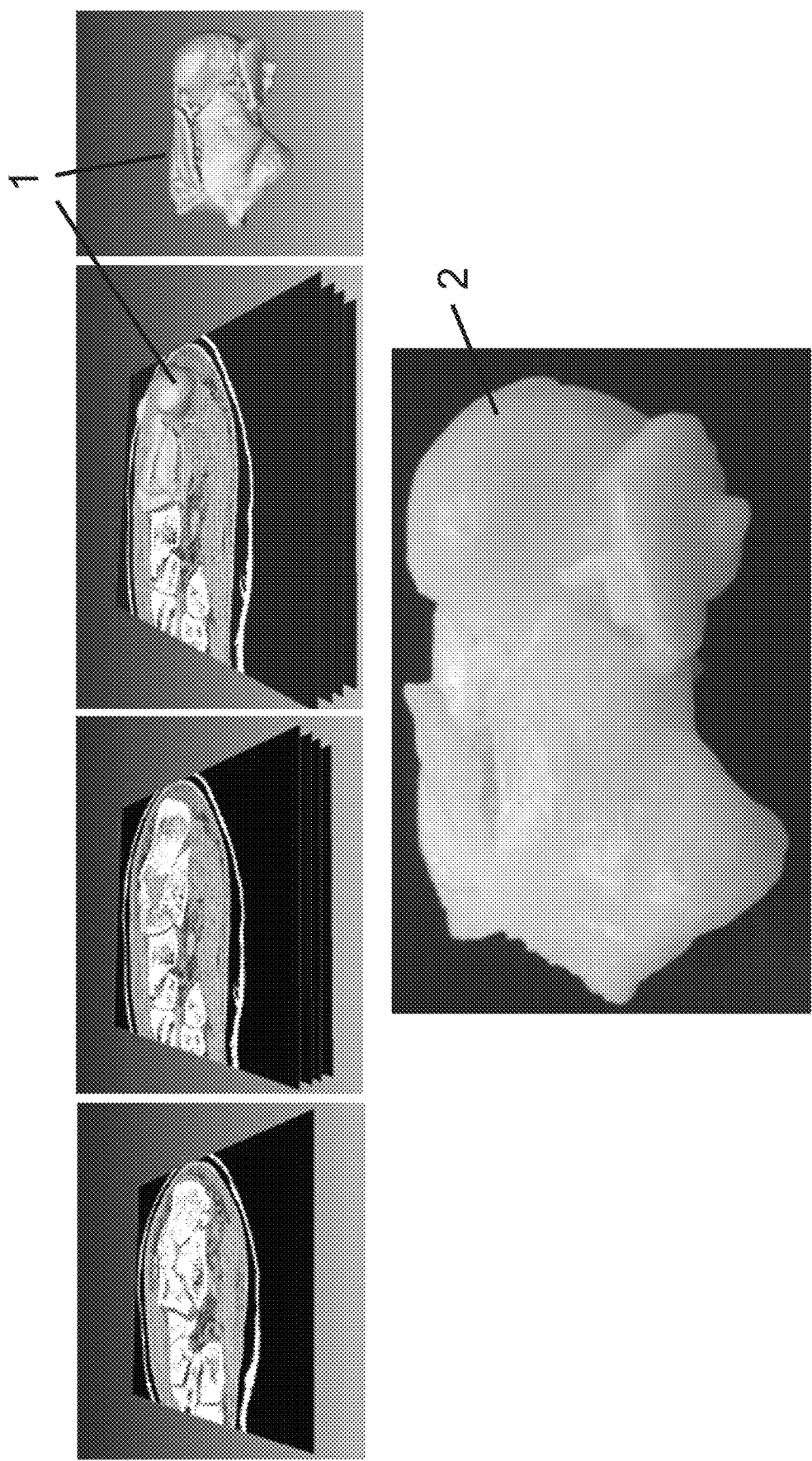
FIG. 1 is a diagram illustrating the Axial3D system.

FIG. 1 illustrates how the Axial3D system uses unique visualization techniques and accurate anatomical knowledge dataset to create a 3D representation (1) of a patient's scan. Medical images are processed and a 3D model is printed to give a 1:1 scale representation of a patient's injuries (2). Hence, the 3D printed model is a reliable model reproducing the patient's exact anatomy and is designed to improve diagnosis and to help plan a personalised treatment for each individual patient. The medical images are often generated by standard medical imaging techniques such as but not limited to CT (Computerised Tomography) and MRI (Magnetic Resonance Imaging).

Figure 2:
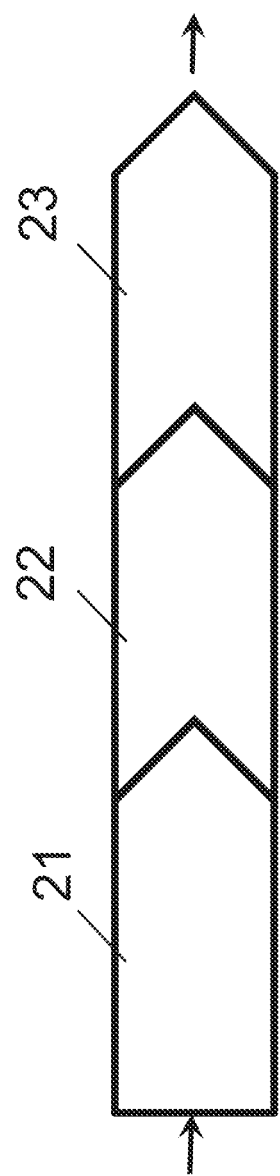
FIG. 2 is a high-level diagram illustrating three basic segments for creating a 3D printed medical model.

FIG. 2 is a diagram illustrating the three high-level segments of the Axial3D system enabling the creation of a 3D printed medical model:

Sending medical images and prescribing requirements or additional metadata (21)

Segmenting images to create 3D printable file of a patient specific anatomic feature (22);

Managing the print process and sending 3D printed physical model(s) (23);

The models produced can be used for a wide range of healthcare applications, such as but not limited to preoperative planning and education. Medical professional, such as surgeons, are able to gain access to 3D printed models as part of their daily routine in assessing treatment pathways for their patients. 3D printable files can be created directly within the hospital through their pre-existing web application without the need to learn how to use cumbersome software that will take hours to segment images.

The surgeons are therefore provided with a much more comprehensive idea of what injury they will be treating, by allowing them to conceptualise the patient's injury in greater detail therefore increasing the effectiveness of their surgeries. This results in improved patient care combined with a reduction in resource burden on the hospital.

Figure 3:
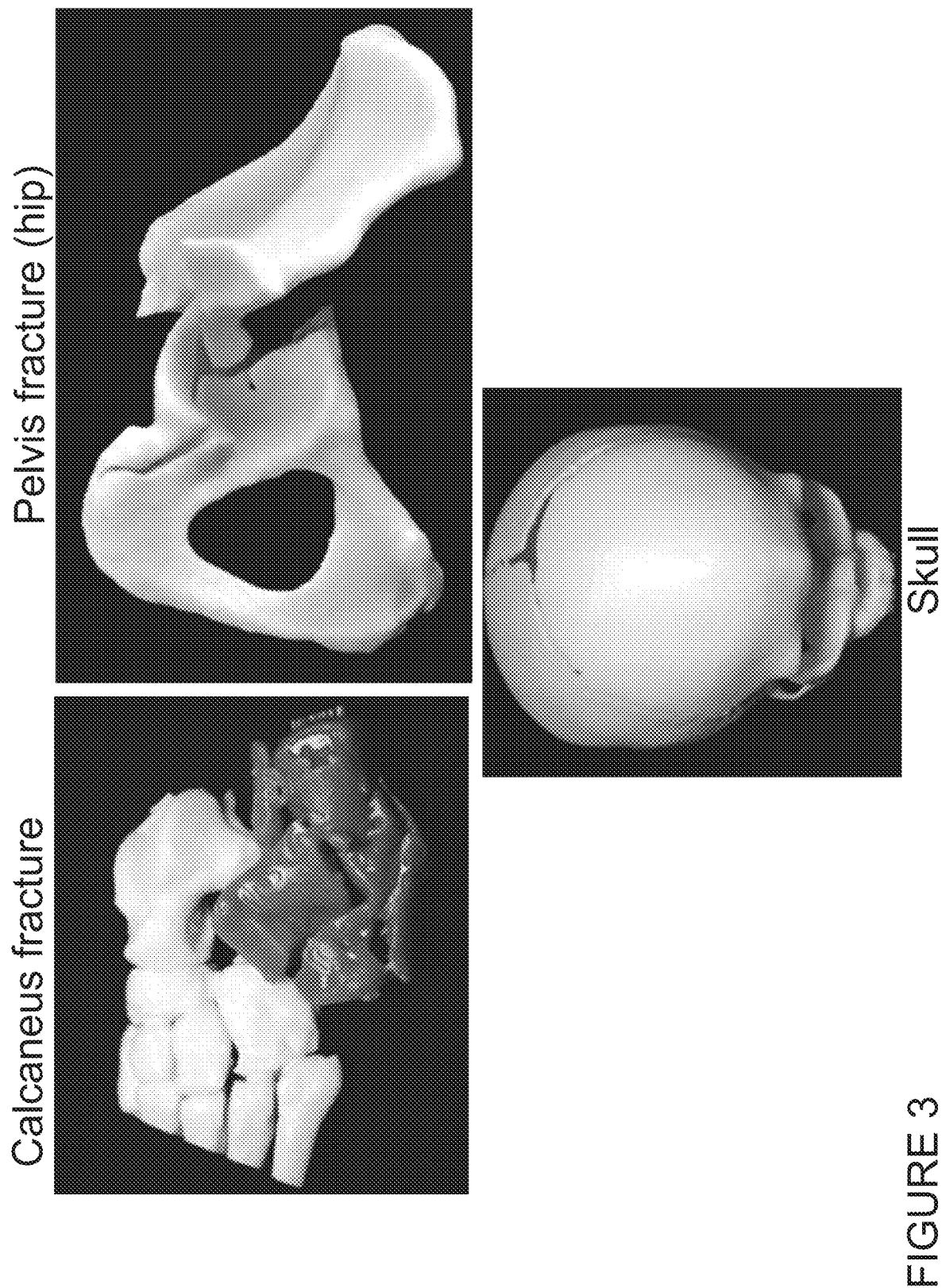
FIG. 3 shows examples of 3D printed model reproducing a patient's injuries, such as calcaneus, pelvis and skull fractures.

FIG. 3 shows examples of 3D printed model reproducing a 1:1 scale representation of a patient's injury, such as calcaneus, pelvis and skull fractures.

The Axial3D system can easily be integrated with the clinical workflows, thus giving medical professionals an easy access to the process of 3D printing that is currently detached from the medical world. Establishing this connection with 3D printing and healthcare is done by automating and refining the processes and creating intuitive, easy to use tools to seamlessly bridge the gap between 3D printing and healthcare.

Figure 4:
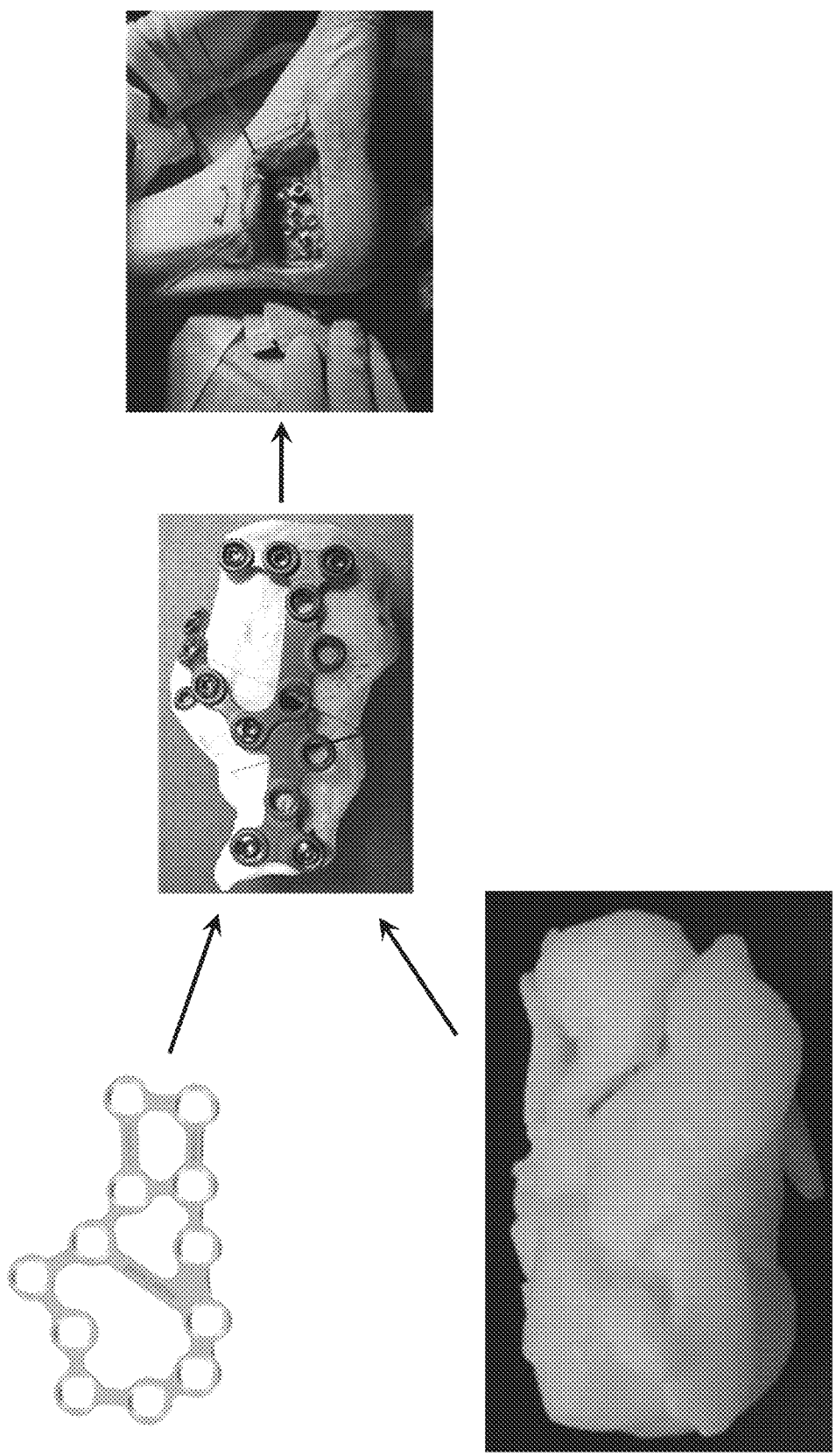
FIG. 4 shows a workflow diagram illustrating how surgeons may use Axial3D for their preoperative planning processes.

FIG. 4 is a diagram representing an example on how surgeons may use Axial3D for their preoperative planning processes in order to speed up surgery times. In this case, surgeons are able to pre-bend and prepare all necessary equipment required to treat a patient well in advance of entering the operating theater, a process that is currently completed when the patient is in surgery. These new methods can typically save around 30 minutes of procedure time, which costs the NHS £60 per minute in direct surgical costs (£1800 per procedure). As the patient spends less time in surgery, they also experience less intraoperative bleeding and a reduce risk of infection. This will then go onto reduce the amount of post-operative care they will require, which in ICU terms can typically cost £2000-£4700 per day.

The Axial 3D system therefore enables healthcare providers to improve patient care and to reduce overall costs. Patient's understanding of operations is also improved and patients are then able to adjust their perception of the risk of operations.

The Axial3D system fills the gap in the market for providing software to streamline the integration of 3D printing into hospitals by providing tools and infrastructure, enabling 3D printing to seamlessly integrate with healthcare systems and clinical care pathways. This allows the customer to manage the printing process from start to finish, within the Axial3D platform, removing bottlenecks in market adoption.

Figure 5:
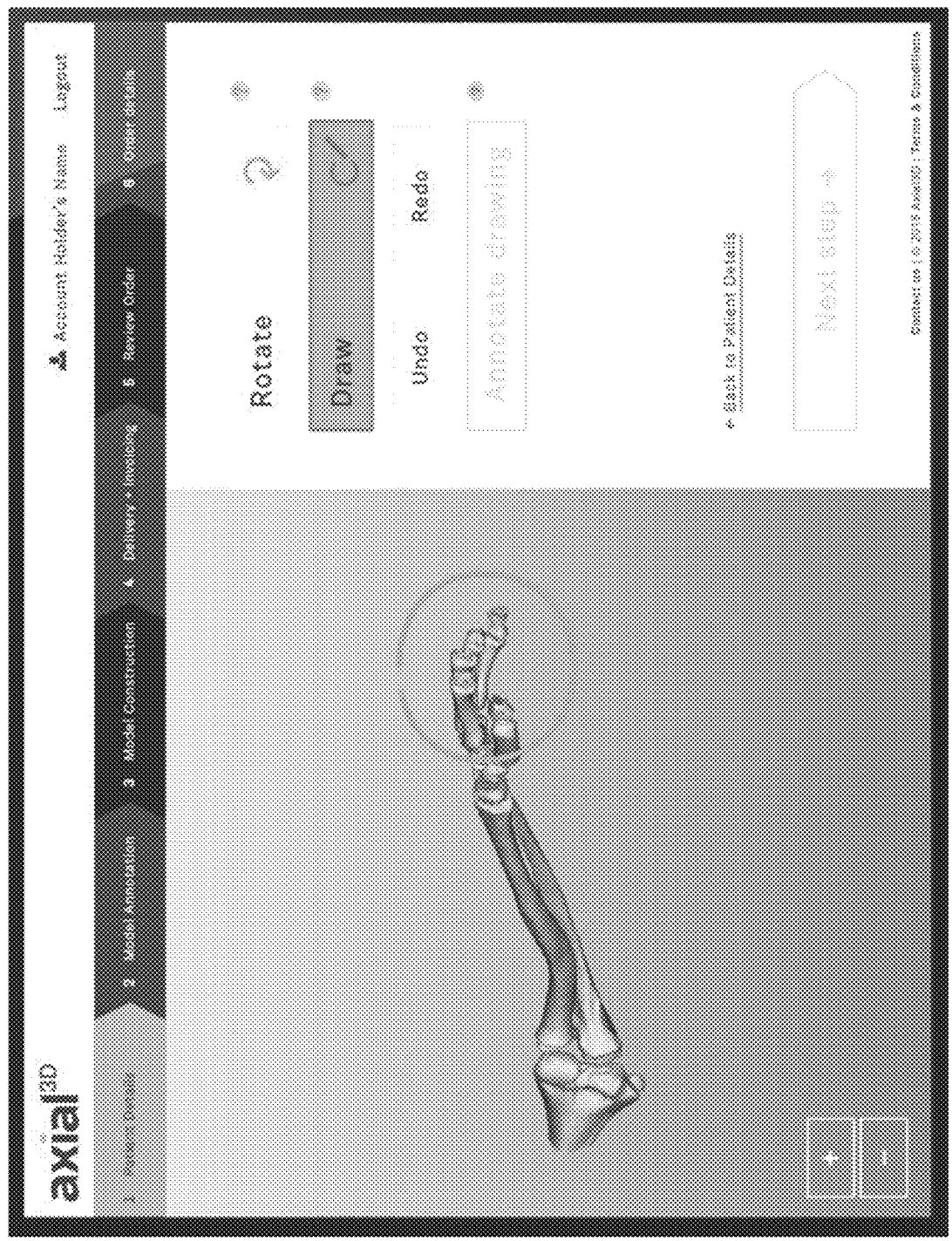
FIG. 5 is a screenshot of the Web application allowing an end-user to upload patient data and order 3D models quickly and easily.
Figure 6:
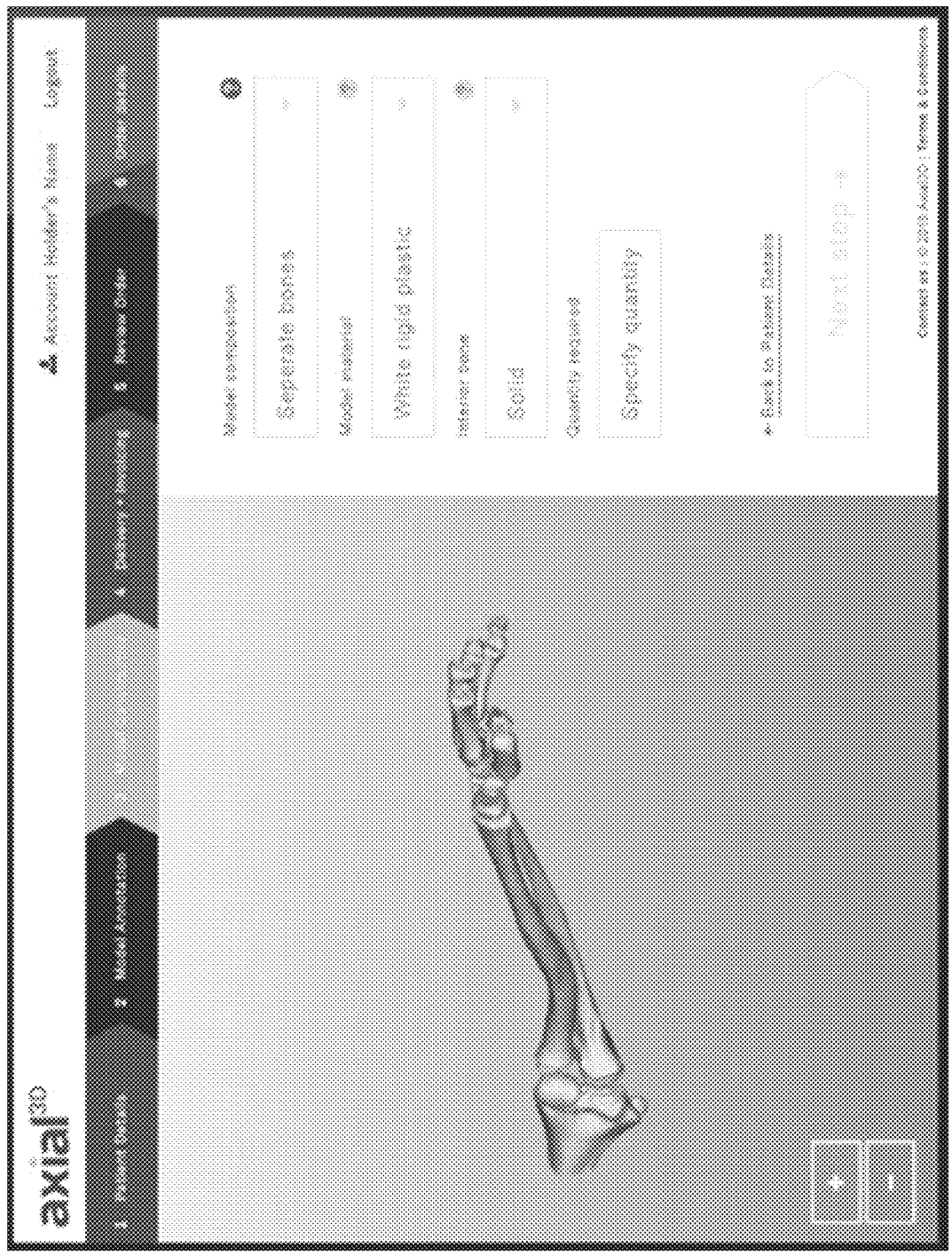
FIG. 6 is a screenshot of the Web application allowing an end-user to upload patient data and order 3D models quickly and easily.

FIGS. 5 and 6 show screenshots of the Web Application allowing an end-user to upload patient data and order 3D models quickly and easily. The Axial3D software automates all of the steps in the process of creating 3D printed pre-operative planning models for use in medicine. The purchase of a model is vastly simplified using the Axial3D system workflow management. For the clinician this lowers the barrier to purchasing. The hospitals are also provided with reporting and user management services allowing them to manage their consumption of models as a whole. Having a web-first platform enables Axial3D to market its services to the global market by mitigating 'the middle man' in collecting the patients' data and prescriptive information.

Unique features include, but are not limited to:

Data science and machine learning techniques are applied to deliver improved 3D models.

Anatomic features are recognised using an anatomical dataset that improves using manual and/or machine learning The service is directly integrated into the medical field.

The need to liaise on a regular basis with the surgeon is largely eliminated.

The workflow guides the user through the order process, from the input of patient details through to anatomy selection and delivery.

A non-technical person is able to order a 3D model.

Surgeons or non-technical person can easily and intuitively upload a patient's data.

The drag and drop interface allows an easy upload of large DICOM (Digital Imaging and Communications in Medicine) image series.

DICOM images that come from a variety of sources (such as but not limited to CT/MRI/PET) may be processed together.

DICOM images which contains unwanted artifacts or background noise, such as foreign objects or a bed, may still be converted and processed.

Development of a DICOM conversion application that takes a series of 2D DICOM images and a scan type as an input. The conversion application utilises a series of image processing operations that detect anatomical regions on each image through automatic segmentation of the anatomy from background.

Thresholding procedure is used for segmentation.

One or more thresholds are applied to the 2D medical images in order to automatically generate one or more different 3D printable models allowing the user to select the printable model with the least background noise. The generation of multiple models is performed in parallel to increase performance.

The Web based viewer allows a user to easily select/annotate the desired anatomy they wish to 3D print.

A preview of the anatomic feature for printing is accessible before the order is completed.

DICOM images are processed in real time into a 3D model for printing through a web application.

Data required to create a 3D printed model is uploaded along with a prescription of specific needs.

The system displays an instant quotation.

Bespoke models are produced in 48 hours or less, which in turns facilitates time constrained procedures, such as trauma.

A surface mesh is generated from the representation of the voxels directly taken from the two dimensional DICOMS.

One or more end-users can have access to the Web Application. The one or more end-users may be assigned different permission or authorization levels.

1. Three Dimensional Printing in Healthcare Management Workflow—Insight

The workflow management software (called the Insight system) makes it possible to routinely employ 3D printing for healthcare providers by making it simple to access the Axial3D tools. The software is available through a web client and a command line API. The Web application allows the user to manage the process of procuring a 3D anatomical model for pre-operative planning and investigation. The Axial3D system also provides reference client implementations (in python and javascript) that allow integration with the Axial3D server Application Programing Interface. The system is capable of receiving medical images from standard equipment. The system then stores those files to enable further analysis and captures annotations to facilitate a prescription for the creation of a bespoke 3D anatomical scale model printed using additive manufacturing techniques. The system monitors the progress of the print throughout the creation process. The system is therefore capable of managing and reporting on the status of the print. Real time information on specific timeframe before a print is ready is also available—taking into consideration the segmentation, surface conditioning and printing. A 3D model can be produced in a matter of hours rather than days and weeks using existing technologies.

The workflow management process is novel in combining a number of emerging technologies to provide a single service. We are using Blockchain to provide secure and anonymous data transfer. Secondly we are leveraging the successes in machine learning as applied to image processing and visualisation to create 3D objects from 2D images. Lastly we are then taking these and preparing 3D printed versions of the anatomical objects. This is a unique combination of technologies that will deliver safe, speedy and secure 3D objects to clinicians in a time sensitive manner in order to allow pre-operative planning. These objects will, in turns, improve the outcome for the patient being treated.

1.1 Upload—One Way Data Anonymisation

Figure 7:
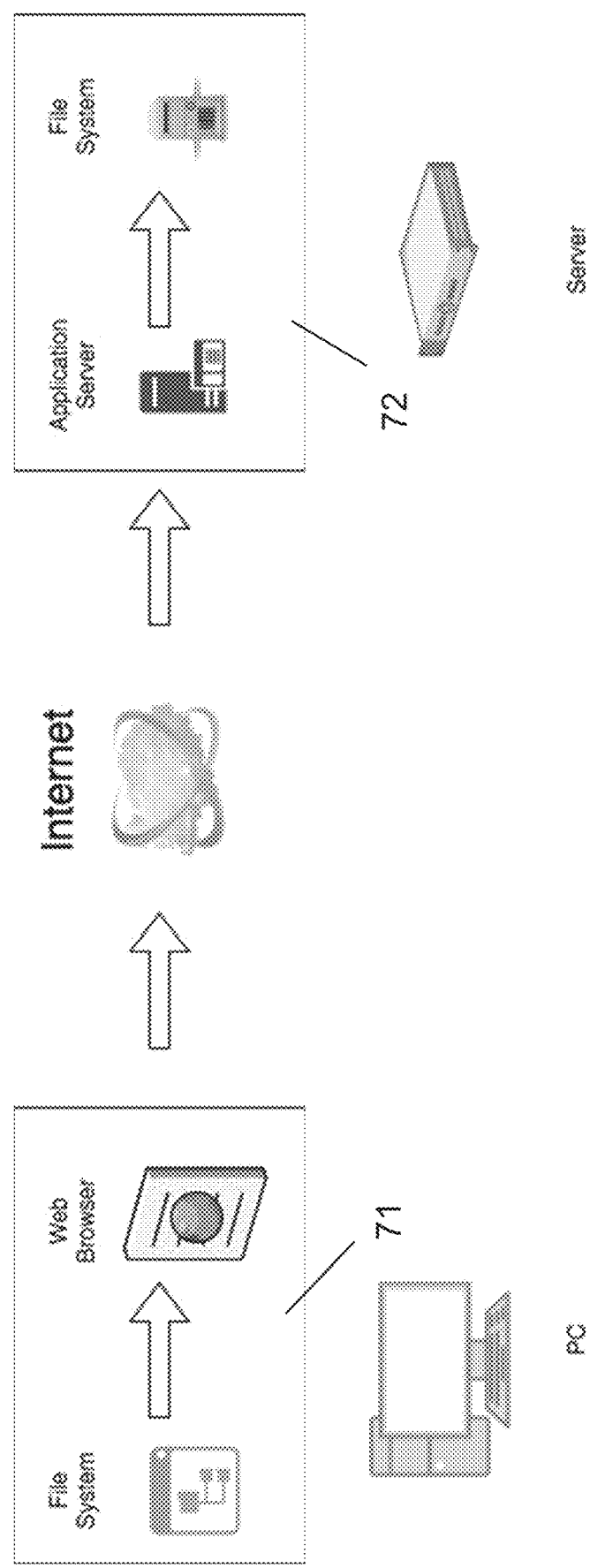
FIG. 7 is a diagram illustrating the workflow for uploading data anonymously.

FIG. 7 is a diagram illustrating the workflow for uploading data anonymously. Data can be uploaded via a reference web application or via command line tools to interact with the API. Data is then scrubbed to remove personally identifiable information from the original data. In this example, the end-user has a file for upload on their PC (71). The end-user can view the files using their File System browser and select them for upload through their web browser. The files are anonymised for upload prior to leaving the user's PC. The anonymised files are then transferred over the Internet to an application server, which saves them to the file system on a server (72).

1.1.1 Upload from PACS

A series of integrations, such as integrating directly with a PACS supplier or a 3rd party client who manages secure exchange of data are provided that allow end-users to send data from their PACS provider directly to the analysis platform to enable the printing of a 3D object. The analysis could be run as a service inside the PACS infrastructure. Or the data could be sent to the Axial3D server for analysis and a 3D Printed object would then be returned. In the case of integrating with the PACS supplier, the Axial3D server would be configured to act as a teleradiology site and receive data directly from the user's PACS system. Where the user has a 3rd party client for data exchange we would provide an implementation of our client software to connect to the Axial3D server and facilitate upload and analysis of the data.

1.1.2 Secure Data Transfer and Handling Through Blockchain

Blockchain technologies have in recent years risen to prominence as a method for the secure tracking and sharing of information. They allow a decentralised and secure tracking system for any data interactions. The architecture allows for storing proof of the existence of data without necessitating the actual sharing of that data. This means it is possible to prove the existence of data or metadata whilst maintaining confidentiality.

For example, this could be the proof that a patient has given consent for sharing of data without the need for us to see the agreement. The information about the consent form and the patient data could all remain on the hospital system and they provide us with the proof that the data exists. Therefore we can proceed with sharing without the need to see the patient information. We only need to see the exact data required for processing.

We leverage this aspect of Blockchain technology for our data sharing platform to ensure that we have received the correct permissions and ordering information from users. We are using Blockchain to build reliable clinical request contracts. Blockchain technology allows us to stand over the inviolability of the data we have received and to proof the provenance of any data and associated metadata. This provides us with the ability to track all events in chronological order. Once the data is received onto the Blockchain it is not possible to alter it. This inviolability principle is crucial to providing assurance about the provenance of information. This ensures that once the conditions for a contract are met it is possible to execute. Hence smart contracts executed on the Blockchain are used to order and/or initiate the 3D printing of medical data.

1.1.2.1 Data Initiation Phase

At the initiation phase, the data plan is agreed by all parties in a smart contract. This allows for the collection of information about the requirements of the prints such as for example: insurance status, payment status/limits, clinician, patient consent, annotations, data sharing agreements and/or data processing agreements. When data is entered into the Blockchain it is time stamped.

1.1.2.2 Print Initiation Phase

Before the print begins, more requirements are added to the 3 dimensional file containing all relevant information for what is required for printing. Information about the stage quality gates is added to the smart contract objects about the print. An example stage quality gate might be added by a quality control technician confirming that the physical printed model matches dimensional accuracy of two dimensional image it was created from. They would be able to add information about the protocol used to make this quality decision—i.e. the metadata about how the data was processed. Once the print object has passed all the required quality gates in a smart contract it is available for printing. A smart contract can execute this stage.

We will receive an encrypted one way hash to initiate an order—This will allow the health care provider to initiate an order, without passing personal healthcare information to the Axial3D. This can be sent to the Axial3D server via the Blockchain and allows for the creation of a smart contract. This contract can be updated with stage gate information as the model is generated by Axial3D.

The Blockchain is also used to record the stage gates that the model passes through during processing, this allows us to automate the initiation of a print once all the required steps have taken place. This means that the network of distributed printers can be controlled via the Blockchain through the validation of a smart contract object in real time.

1.1.3 PCoin

The Blockchain infrastructure facilitates the exchange of information and data required to implement the printing of an anatomical model of patient data. Printing out a file also requires the utilisation of our currency—PCoin. By linking the printing of an object to the PCoin we ensure that the requirements of the smart contract are validated. Users of the printer are motivated to ensure the validity of the Blockchain and the smart contracts as are those requesting the prints.

This linking of the physical product to the smart contract on the Blockchain allows for internally consistent pricing of the transactions and contracts.

Leveraging the Blockchain like this allows us to treat it as a safe deposit box, allowing handover of privileges. It is the ultimate audit trail for verifying that steps have been executed by parties in an agreement (smart contract). We enable the ability to encode the properties of the data that is printed into a physical 3D printed object and a virtual record stored on the Blockchain. This is facilitated by a QR code embedded in the 3D printed object and stored with the digital record. This allows the linking of a QR code to a specific print. The process of hardlinking is described in more detail below. Properties that are recorded include the 3D representation of the printable object and the information about the steps carried out by the Axial3D server to create this printable object. Therefore it is possible for anyone to verify that the appropriate quality control operations have been carried out.

Print scheduling can be operated and managed using a DApp executing smart contracts. This would be a Blockchain based application that sits between the data processor and the printer detecting when prints are ready to be sent to the printer. It is capable of identifying when the criteria for printing have been met and of deciding how best to arrange the printing on one or more printers.

Hardlinking allows for the linking of the original order, including the smart contract and data (e.g. image scans and user specifications) to the physical object used by the clinician and the auditing of all of the modifications of this data. Key to the print management process is the transfer or realisation of the software defined print in the physical world. In order to track the transition a number of techniques are employed to hardlink the software pipeline to the physical object produced on the printer. The aim of these techniques is to create an object hyperlink. This hardlink is capable of being represented in a number of different ways. It can be a simple computational hash of the output of the software pipeline. It can also be embedded into a Quick Response (QR) code, NFC chip or RFID tag. This system allows us to move between the virtual world that created the 3D printed physical object and the physical world that the object is instantiated in.

QR/Compliance code for tracking 3D printing is an inherentiy digital process. We are generating a digital supply chain. Every part and process or modification is documentable and attributable. This creates opportunities for tampering and theft. We have the ability to trace the objects from order initiation through to production and potentially to usage/implantation. Through hardlinking a single object is provided from conception to implantation. Hardlinking is the registration of a unique code to a single print—covering the entire pipeline from initiation to print. This system provides the infrastructure and oversight necessary for the management of a 3D printing facility to provide anatomical scale models from medical images. The system allows users to upload medical images directly and annotate those images in the workflow. We provide a reference implementation via a website and a command line tool that accesses our application programing interface.

At the initiation of an order a cryptographic hash of the patient information is created by the ordering organisation. This allows them to identify a patient without passing over any sensitive patient identifying information. This is crucial for the system as it allows the organisation placing the order to validate for itself that the model printed is associated with the correct patient without disclosing the patient data.

1.2 Print Management

Tools are provided in order to determine if a given volume is printable and to identify problems with the printability of the object. Based on an understanding of printing volumes rendered by computational or manual techniques, the printability of 3D physical model of a patient specific anatomic feature has been extensively studied and understood, such as: how to print a diverse set of objects within a scene, the management of printing a diverse set of objects, including the ordering, orientation, placement on plate and across multiple types of printer and printing technologies.

Connected machines may also operate in conjunction with each other to create a required 3D print. This requires a coordination layer sitting between the image processing algorithm and the printer to determine the optimal print delivery pipeline.

Text messaging may be used to report on status and initiate commands to the server.

1.2.1 Scheduling of Prints

Print scheduling is used to facilitate the volume and timing of print. Timelines for prints are scheduled based on prints finishing within a 10 hour working window and based on inbound models and surgical requirement. Delivery schedules are also based on achieving lowest cost for arrival of an on time model.linked with the cost of the postal service and provider, as well as method of transportation, including autonomous vehicles known as drones. In each case, an equation can also look for models that can fit within its print volume for a single print.

Some examples below are given, in order to meet the required date N for the delivery of a 3D printing model:

$$\text{Model required date} = N$$

i.e. If N>72 hours from upload—lookup—N<72 days if no prints and schedule 48 hour royal mail pick up if UK—if EU US schedule 48 hour DHL US & EU;

if N<72 hours lookup—instances for N<48 hours—if no prints and schedule 24 hour royal mail pick up if UK—if EU US schedule 24 hour DHL US & EU;

if N<48 hours lookup—instances for N<24 hours next available printer slot and schedule—if no prints and schedule 24 hour royal mail pick up if UK—if EU US schedule 24 hour DHL US & EU;

if N<24 hours lookup—next available printer slot and schedule drone pick up=length of print time+120 minutes;

If N<24 hours and not within drone/unmanned vehicle range complete if statements above to the closest geographical location of print farm to delivery address of order.

1.2.2 Automated Material Selection

Different parts of the anatomy require different approaches to 3D printing. The printing of multiple pieces of anatomy in a single print or combining them requires the construction of bespoke printing strategies.

To meet the expectations of users of the 3D prints, the selection of the materials used are optimised to print the anatomical features for their resemblance to the material used for printing. For instance hard bone is printed in harder materials and soft tissue in softer materials. Hence, the software automatically selects the material for printing. This selection may also be based on the requirements of the model, e.g. speed with which it is required.

There are restrictions on the possible size of the prints using existing 3D printing machines. To overcome this for oversized pieces of anatomy we construct custom features that allow the combining of multiple 3D prints into a single 3D printed model. The placement of these connective pieces follow a set of rules that which have been formalised such that they can be applied also to new models. To achieve this, the Axial3D system is able to predict the type of material required for these connective pieces.

1.2.3 Automated Printer Selection

Depending on the type of anatomy to be printed we will select the material and technology pairing best suited to the final model. This relies on the ability to clearly identify the anatomy beforehand. An input to this process is a pre classified piece of anatomy (taken from the medical scans) which is present in the object or objects to be printed. The output of the process is a selection of the specific printer that is best suited to the anatomy being printed. Printers have the following dependencies: build volume, materials available, minimum feature size. The parameters involved in the selection of the 3D printer are: volume of 3D model, hollow structures within the model & minimum feature size. The algorithm matches the printer parameter to the model parameter as described above.

We have built up a series of profiles of users and their preferences for particular model types. For example we have data that indicates that oncology users prefer prints that can incorporate clear models. We will use this information to predict what kind of technology the model should be printed on for the user's requirements.

1.3 axial3D Automated Pipeline

Figure 8:
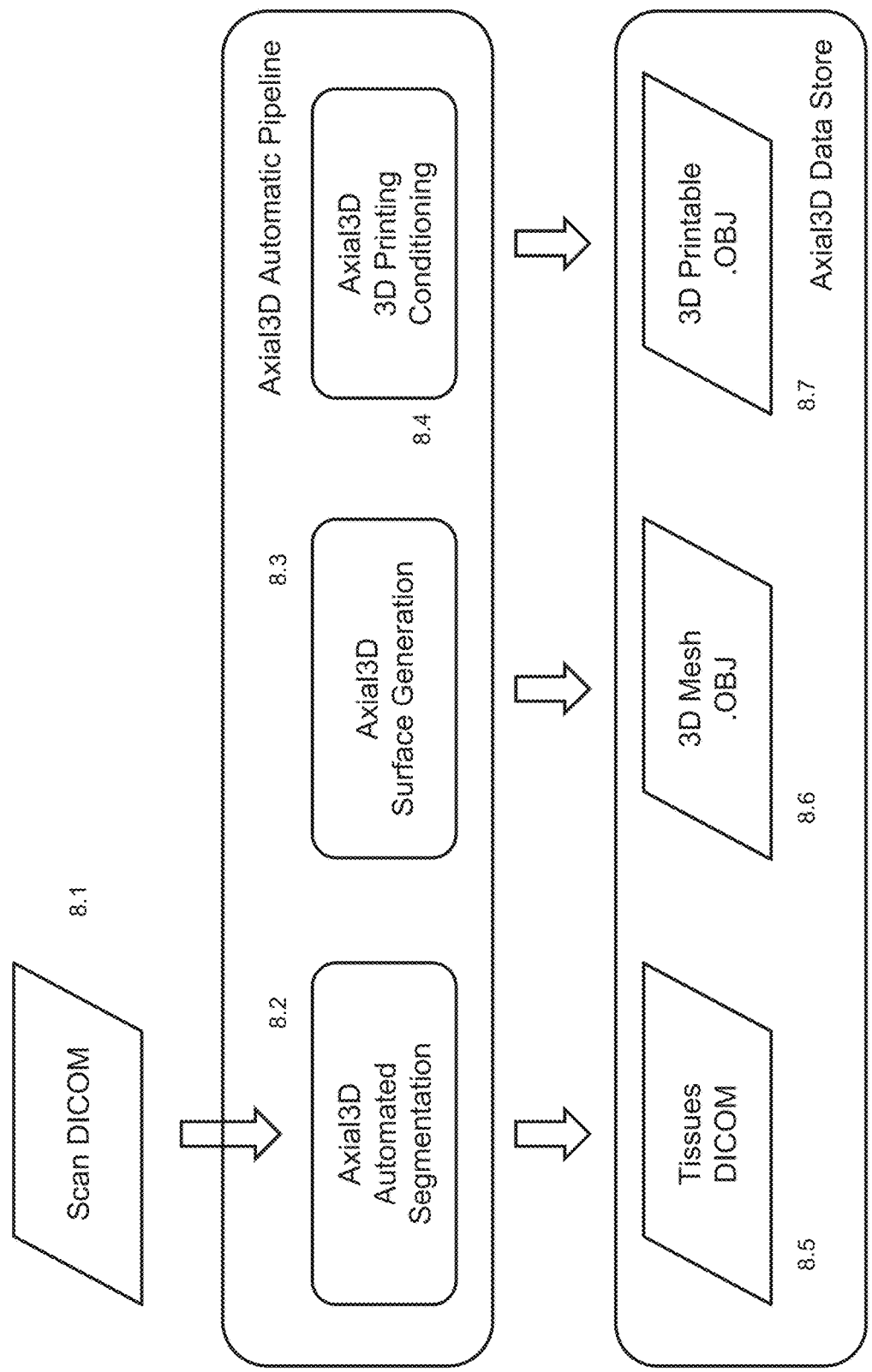
FIG. 8 is a diagram illustrating the workflow from receiving the data to displaying the data and obtaining 3D models ready to print.

FIG. 8 shows a diagram illustrating the Axial3D Automated Pipeline workflow; once the data is received (8.1), the Axial3D automated segmentation will identify the anatomical components within the scan and "label" them accordingly (8.2). The Tissue and Organ Segmentation is then used by the surface generation in order to create the organ volumes (8.3); the volumes are then passed to the conditioning phase (8.4) which will identify the volumes that require printing, the associated correct materials and perform the printer selection. The three objects produced by the Axial3D Automated Pipeline stages are used in different ways: the segmentation data and the 3D Mesh produced by the Segmentation and the Surface Generation stages (8.5 and 8.6 respectively) are used in the Axial3D review component of the Web app; the user can interact with them by adding annotation, select components to be printed and select preferred materials for specific anatomical features; the 3D printable object (8.7) is used at print time. All output files and data are stored in the Axial3D Data Storage and can be downloaded using the Axial3D CLI. All steps are described in greater details below.

1.4 Model Annotation

The user is presented with the 3D model that is generated using the steps described in the automated pipeline. This process identifies pieces of the anatomy visible in the scene. This allows the user to interact with the 3D model on screen. Once the model is shown on the screen the user can zoom in and out to visualize the model as well as provide annotations. These are free hand drawings that are mapped onto the model by our software. It is possible for this annotation process to be completed on a mobile as well as on a desktop or on other devices.

The annotations provided by the customer are then used to, for example:
  1. clearly and accurately define regions of the scene that they want to print;
  2. provide information about the anatomical components contained within the scan, facilitating the task of anatomical identification (see below).

1.5 Image Manipulation and Download

Protocols for the handling of data by expert medical visualization engineers have been developed. In addition, tools for the exchange and storage of data and annotations generated by the healthcare professionals have been developed.

It is possible in this view to overlay the 3D models, and the original scans as well as the automatic segmentation results in order to facilitate validation of the segmentation algorithm. Through the web application the results of the automated segmentation are presented and the engineers are able to approve the segmentation. Tools and an interface also allow the modification of the segmentation within the Web App.

Methods are also developed to increase the speed of transfer of data about medical images including specialized formats and data structures. This includes the identification of duplicate information prior to data transfer, enabling only the sending and receiving of unique information. Hence less information needs to be sent, resulting in faster transfer times. This is key to ensuring that users experience faster loading times and a better user experience. This requires the development of infrastructure that enables the storage of a large amount of data routinely. This also requires significant investment in security to ensure that patient data can be handled safely and securely.

Post image analysis, it is possible to download annotated medical image files. These contain the output of our automated segmentation algorithms. They can be viewed in a standard medical image viewer. These images are copies of the original.

1.6 User and Task Management

Figure 9:
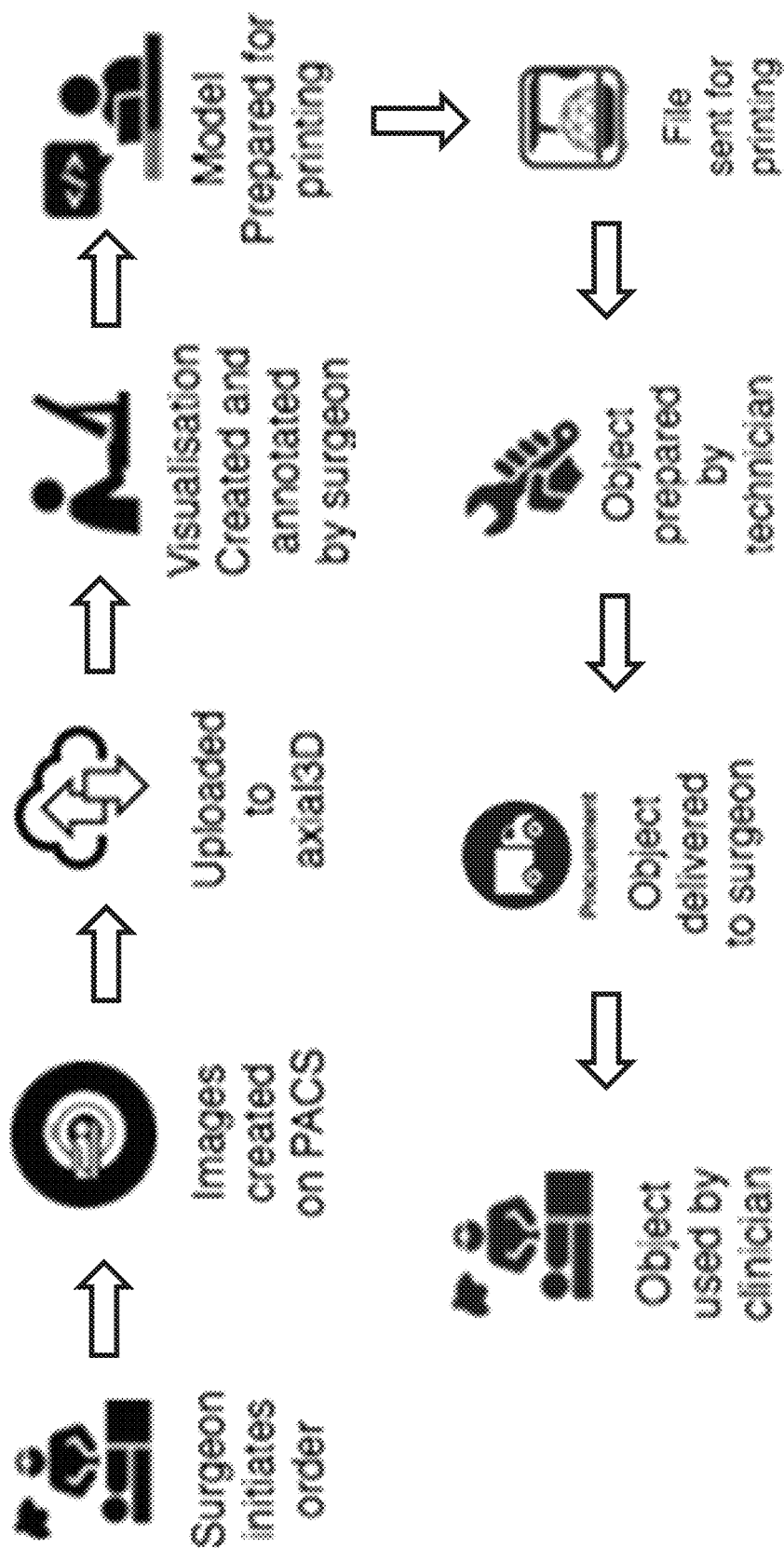
FIG. 9 is a diagram illustrating the main aspects of the workflow.

FIG. 9 is a diagram illustrating the main aspects of the workflow from the surgeon initiating an order to the delivery and utilization of the 3D printed model by the clinician or healthcare professional. The process of ordering and generating a 3D printable file and subsequent printing of it can be broken down into a series of one or more tasks. Each of these tasks can be carried out by a person or automated. We provide the infrastructure, services and software as well as management interface to facilitate the implementation of these tasks. We offer a task-based approach to executing the process of creating a 3D anatomical model. We allow multiple users from an organisation to participate in the process. This is in addition to the use case of a single user operating the entire workflow on their own. This encompasses image processing specialists who can interact with the data upload stages. Medical professionals can upload data about the model being created and annotate the model as it progresses through the workflow, as shown in FIG. 9.

We support all aspects of the ordering process within a healthcare setting. Our software allows the role based provisioning of the tasks required to order a 3D print. From the surgeon requesting the print, anonymisation of the data uploaded by a radiologist, sign off on the spend by clinical director, procurement decisions by the healthcare provider, transfer of files from the imaging systems, management of the 3D print process internally and tracking all these authorisations within the system. The tracking facilitates the production of an audit trail capable of providing the required information about the transition of the data through the workflow into the final 3D printable object. The workflow management software holds all user types and assigns roles appropriate to the user controlled by the group administrator.

Users can be grouped together for example by membership of the same organisation or group of organisations. In this case an administrative user must be created to manage roles and access.

1.7 Improved Healthcare Experience Through 3D Printing

Patients experience an overall improvement of the level of service provided by the healthcare institution when 3D printed models are used. The models can be used by the medical staff to improve the communications of the conditions to the patient, allow a more informed decision as to the course of treatment to be followed as well as improve their confidence on the medical staff and institution caring for them. This will lead to increased buy-in by the patient thereby.

2. Axial3D Automated Segmentation

The goal of image segmentation is to assign to each pixel within a digital image (volume) a label corresponding to a given class (bone, fatty tissue, tubular tissues such as veins and arteries, tissue with cavities such as lungs, etc) of possible objects that may appear within the image. The classes may represent any kind of object that may appear within the image, including human tissues, organs and foreign objects (the scanner bed, metal implants, pacemakers etc). This means that we take medical images as input and produce a new volume superimposed onto the original scanned volume where each pixel of the original volume is replaced by the label corresponding to the appropriate tissue type.

This section will outline the algorithms implemented by the Axial3D server in order to achieve accurate and reliable segmentation of the medical scan for the purpose of 3D printing. Each algorithm has a number of advantage and disadvantages. The segmentation pipeline includes a final step where the results of all algorithms are combined together to derive a final segmentation that is then used to combine the results of the various algorithms.

Figure 10:
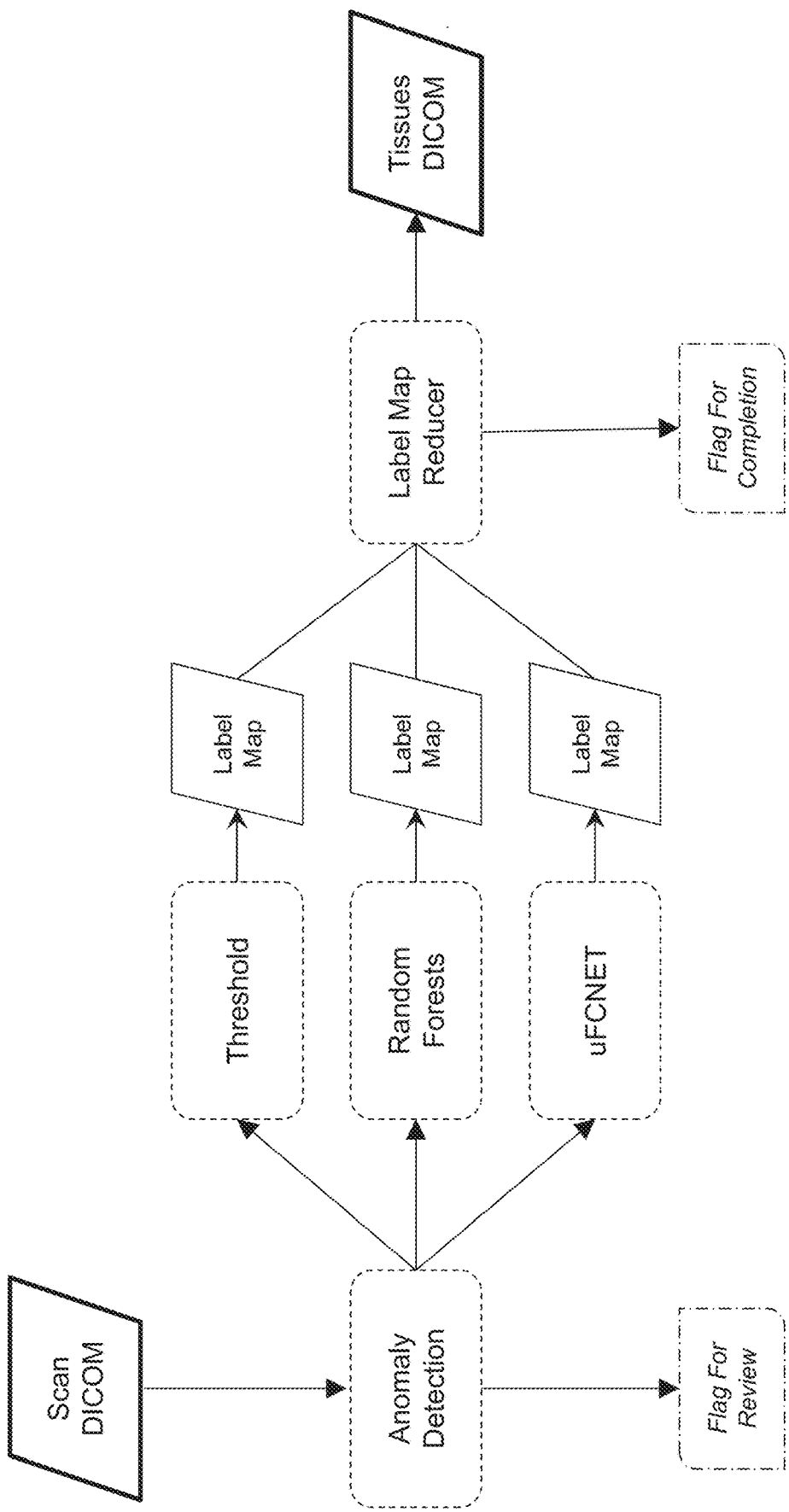
FIG. 10 is a diagram illustrating the automated segmentation workflow.

FIG. 10 shows the Automated 3D Segmentation workflow. The input data, consists of the scan DICOM stack provided by the customer; the stack contains the 2D images obtained from the medical scan; automatic anomaly detection will flag the presence of gross anomalies and inconsistencies in the input date; the data is then passed to any number of segmentation algorithm (three shown in this example), each algorithm is run independently from the others; each algorithm produces a segmentation map; the results of all Segmentation workers are then combined by the Reducer; the final Label DICOM stack is then outputted and passed to the 3D surface generator code.

2.1 Anomaly Detection

Anomalies and erroneous information are often contained within the data that is received with the patient order. Such anomaly present itself as a mismatch between the expected form of the date and what is being received; this mismatch may appear both as a gross or very subtle deviations from the expectation. Anomalies are any form of deviation from the expected appearance of a scan that would impair the results of any of the automated algorithms and lead to incorrect 3D models.

Possible sources of anomalies are:
1. human errors such as: scan data may be classified as a computer tomography where in reality it is an MRI scan or incorrect patient data;
2. presence in the scan of foreign objects that causes aberration and errors in the scan data;
3. low quality scan images dues to issues with the scanning hardware or inconsistencies in the scanning protocol (wrong X-Ray energy and flux; wrong scanning settings used during the scan; worn out X-Ray source and/or other equipment);

The automated pipeline will detect these anomalies by comparing the information provided against a simplified standard set of parameters expected within the 3D volumes; this standard implements a number of simple rules on the expected color histogram to check against: for example, CT scans will generally display strong components in the region of −1000, −80, 80 Hounsfield units roughly corresponding to fatty tissues, tissues containing water and air; the lack of all these three components will indicate that the scan may not be CT as specified by the user. The same applies to MRI scans. Detection of such cases will result in marking the scan for revision by an engineer in the workflow.

2.2 Threshold

Figure 11:
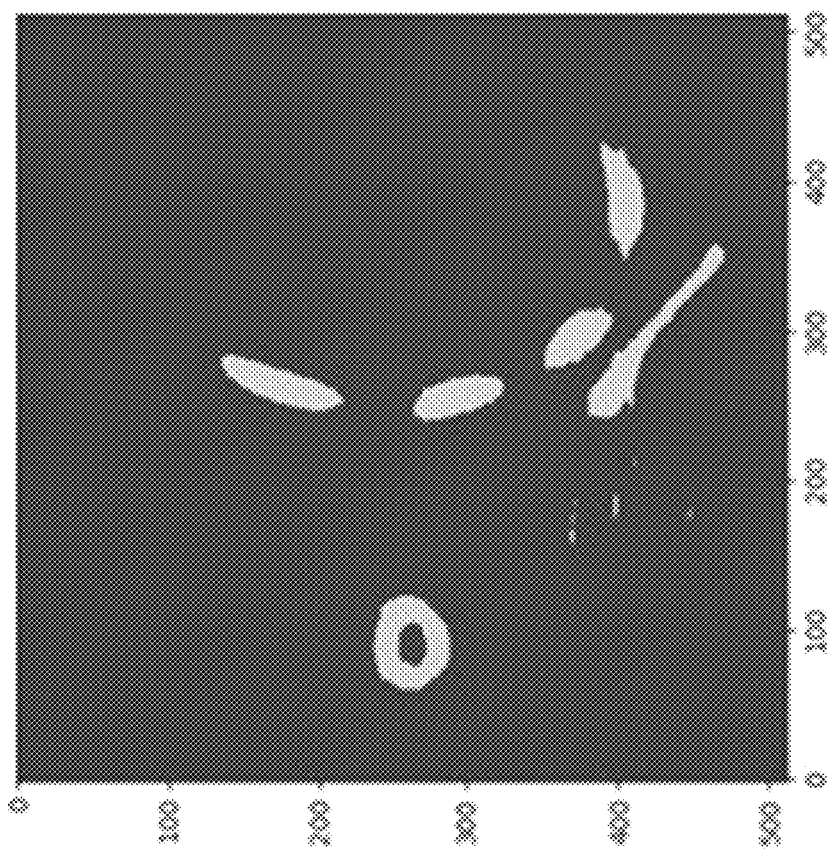
FIG. 11 is an example of medical image segmentation using a threshold estimate.
Figure 11:
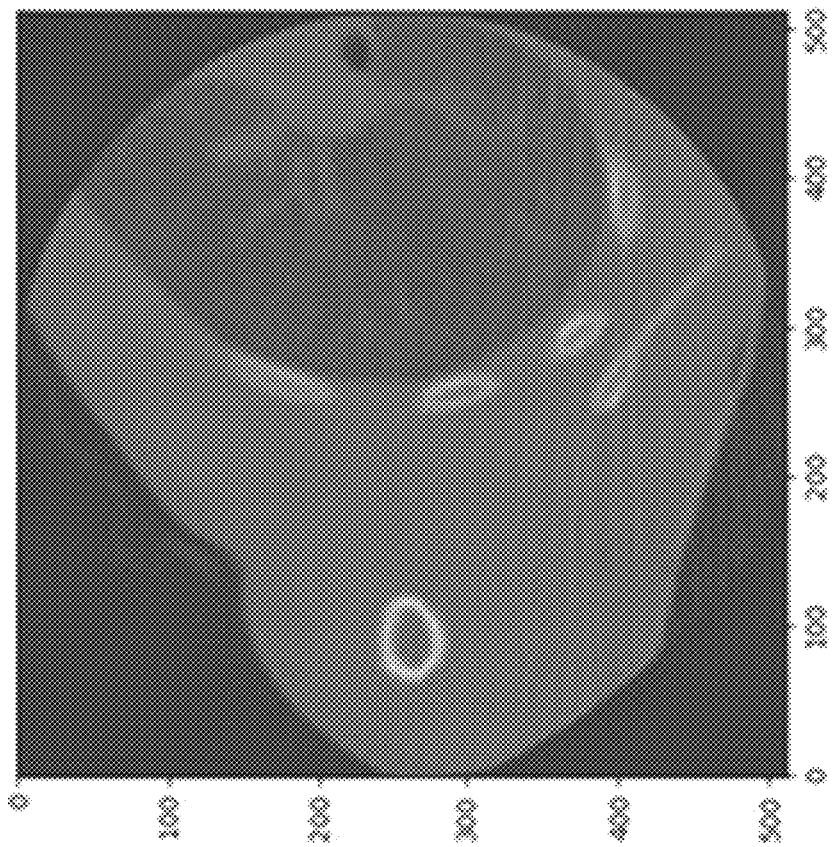

The simplest method of image segmentation is to use a thresholding algorithm based on the knowledge of the typical Hounsfield of bones. FIG. 11 is an example of medical image segmentation using a threshold estimate (see below for an outline of the automated threshold estimation algorithm). In this approach, all pixels with a value above 193 are classified as bone, while pixels below this value are non-bone.

The Axial3D threshold algorithm expands on this concept by using a logistic probabilistic function instead of a hard threshold in order to calculate the likelihood of a pixel of being the tissue in question instead of a binary value, e.g. instead of "bone" VS "no-bone", the threshold calculates a value between 0 and 1 where higher number corresponds to likelihood of being bone).

The main issues with this method are:
1. Noise of non-bone tissue: it is often found that non-bone tissues may light up and appear as small regions with pixels with values above 190; this is often caused by the limitation of the imaging technology (the 2D tomographic reconstruction in particular) which may create small artefacts;
2. holes in bones: for the same reasons discussed above, it is very common for small regions (typically 5-10 pixels in size) of bone to appear dimmer within the image (less than 190); these regions appear as holes in the bone;
3. foreign objects: it is quite common to observe foreign objects within the CT scan such as the bed onto which the patient is laid; these object often have very high Hounsfield Units (HU) due to their relatively high density; these objects are often segmented as bone due to their large size and high pixel value.

The issues described above are partially mitigated using a smoothing algorithm (Gaussian or median filtering); such methods improve the overall quality of the segmentation however will slightly reduce the fidelity of the bone volumes.

Thresholding in combination with a small pre-processing filtering (Gaussian) has been found to be the most appropriate method of image analysis for the generation of Web-App models. The models have acceptable anatomical fidelity as well as a very low number of mislabelled bones as a relatively small number of holes. All anatomical features are present, with the exception of very small bones such as carpal feet and hand bones, in particular in proximity to the physic and maxillofacial features in children and in elderly people (in particular subjects with advanced arthritis).

2.3 Programmatic Threshold

We have demonstrated that it is beneficial to apply different parameters as inputs to our algorithms on the basis of the application area. Specifically, we have optimised the creation of the model based on key parameters such as the scan type, bone type, tissue type, age, gender and weight of the patient. We capture this information from the images and by capturing this in the user interface to our software.

The Scan Type and Bone Type of the DICOM image series are key parameters that provide information that is used to make the threshold process more robust and accurate. The end user selects a Scan Type (ST) of CT, MRI, PET or SPECT and a bone type (BT) of Hard or Soft. The threshold step segments out the bone from background information e.g. skin and foreign objects such as a bed. It is critical that all of the bone (and only the bone) is segmented during this .step. Failure do this will generate an invalid 3D model.

A considerable amount of work has been carried out in order to determine the best threshold value to be used for a given CT scan. It has been found that the ideal threshold varies depending on the CT scanning parameters (X-Ray energy and dux); these settings are ordinarily modified by the radiologist performing the scan in order to maximise the quality of the scan.

Figure 12:
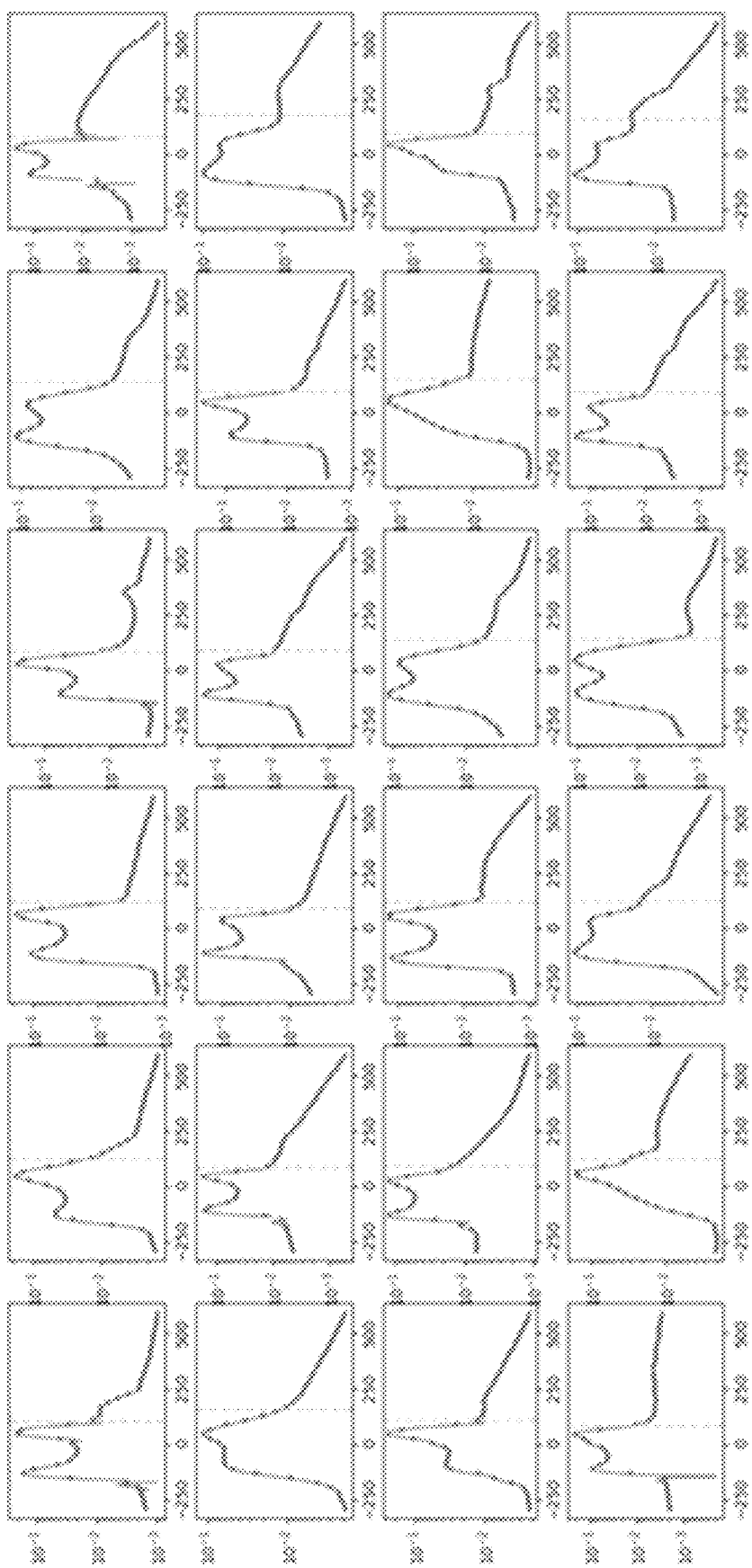
FIG. 12 shows images displaying the bone threshold estimated using our method for the Hounsfield unit histogram from 24 CT scans.
Figure 13:
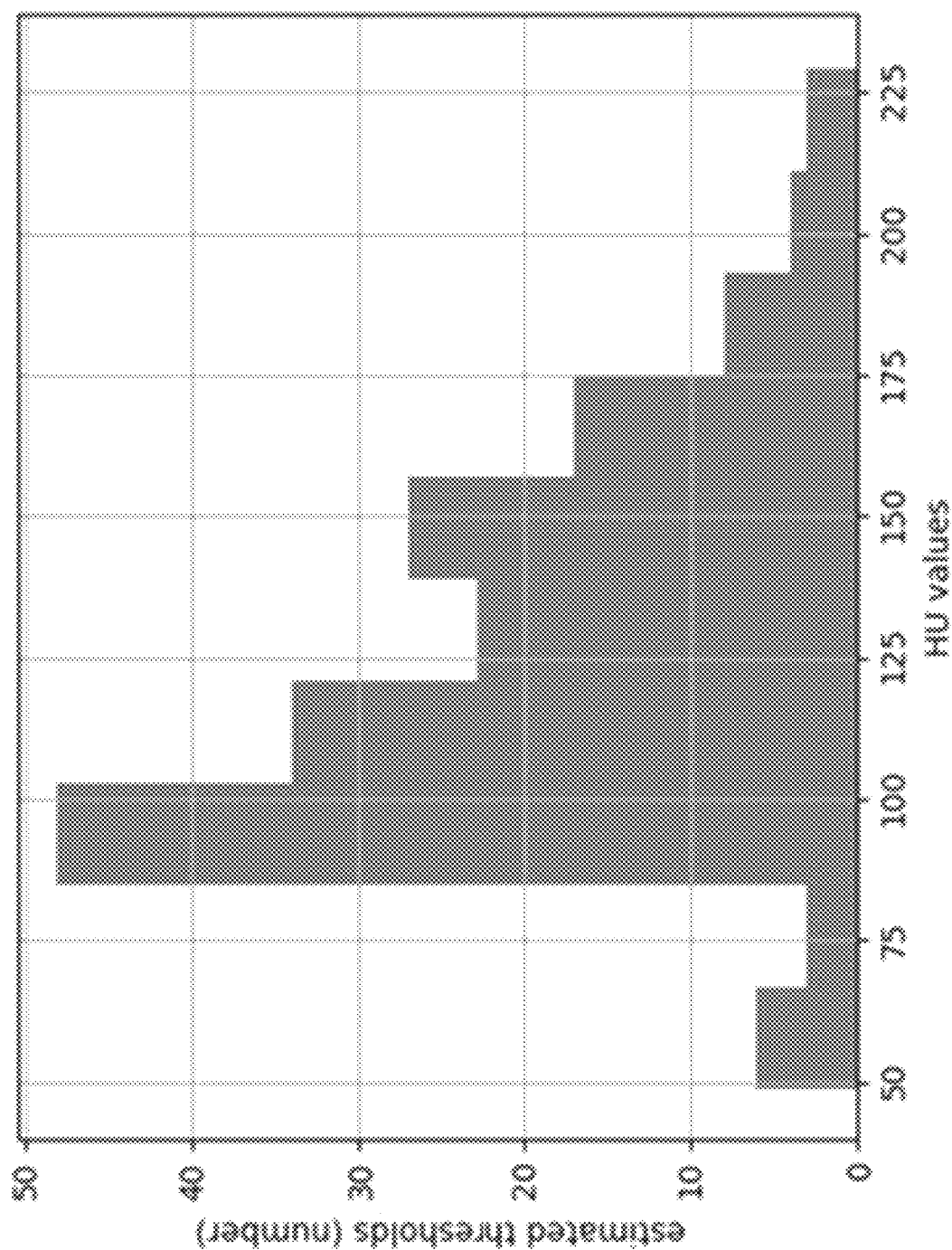
FIG. 13 is an histogram of the threshold across 175 CT scans.

In order to obtain the best segmentation results, the Axial3D Automatic Threshold Estimator uses an analysis of the scan color histograms in order to derive the best estimate. The algorithm performs the following steps:
1. detects the peaks of the histogram corresponding to the tissues that are similar in color compared to the tissue of interest;
2. once the peaks are detected, their infection points are derived by calculating the zero of the histogram second derivative in proximity of each peak
3. the offset between the peak and the inflection point is derived;
4. the estimated threshold corresponds to the position of the peak with an offset corresponding to three time the inflection offset;
5. if an error occurred during the peak detection, a default threshold is used depending on the tissue of interest and scan type; errors include the lack of peaks in direct proximity to the tissue of interest, peaks may not be sufficiently prominent (too small); the scan modality and/or tissue type may not be supported by the algorithm FIG. 12 shows the bone threshold estimated using our method for the Hounsfield unit histogram from 24 CT scans. As it can be seen, the 24 histograms vary considerably; this variability is due to the varying ratio of different tissue type within each scan as well as the CT scanner settings (voltage, flux etc). FIG. 13 shows the histogram of the threshold across 175 CT scans. The histogram shows the variability of the estimated threshold; for the majority of scans the estimated threshold is around 100 Hounsfield unit; this is the lowest threshold value that can be used in order to remove all non-bone tissue from the segmentation results.

2.4 Decision Forests

Decision trees are an improvements over the threshold method described above. They involve the creation of a "tree of thresholds" where pixels are classified based on a number of properties, not just their value. Any property of the pixel as well as its neighbours can be used to create a new decision.

In the context of our application, the following properties of the pixels have been selected in order to create the decision tree:
1. how many pixels looking almost like bone are near the pixel in question;
2. how many pixels looking exactly like bone are near the pixel in question;
3. how strong is the overall gradient of the image at the given pixel if the consistency of the gradient direction within a small neighbourhood of the pixel; Sobel filters are used in order to derive this property;

The decision trees are trained using existing pre-labelled Axial3D patient data. The decision tree is applied to a subset of pixel within the original scan; the labels obtained from this subset are then up scaled using standard interpolation methods in order to recover the segmentation of the full image. The pixel subset is generated by subsampling the original images, typical subsampling strides are 5, 7 or 13 in both the X and Y direction. The subsampling stride is selected depending on the pixel size (derived from the DICOM themselves); the subsampling stride is selected so that the subsampled resolution does not fall below 5 mm in the original space.

Figure 14:
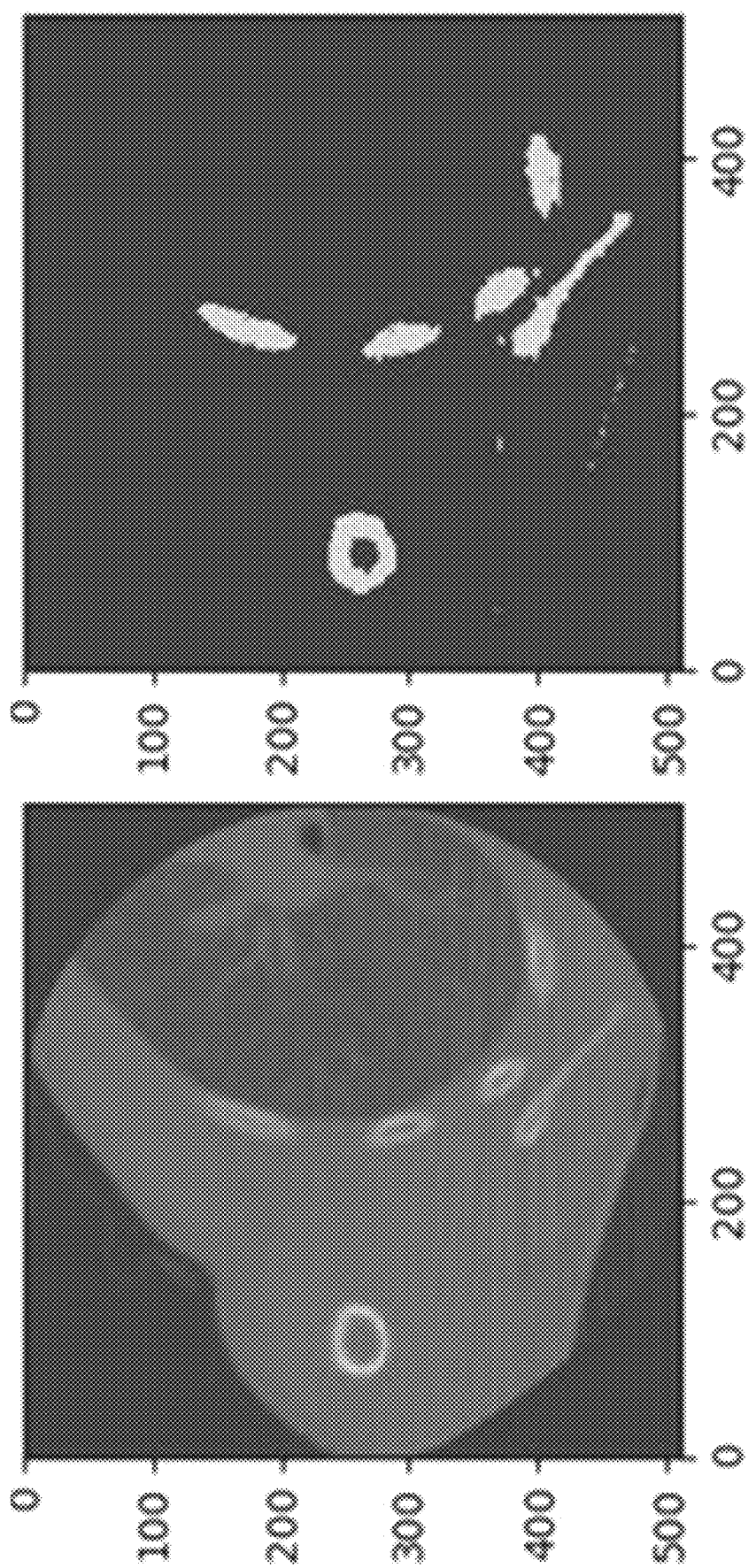
FIG. 14 is an example of medical image segmentation using random forest.

FIG. 14 is an example of medical image segmentation using a random forest. Decision Trees produce lower fidelity segmentation compared to thresholding algorithm(s) (the edges of the anatomical components are not as accurate), however it produces less noise.

2.5 Chained Decision Forests

In order to overcome the poor resolution of a single decision tree forest approach, a new approach based on a hierarchy of decision forests is developed.

Figure 15:
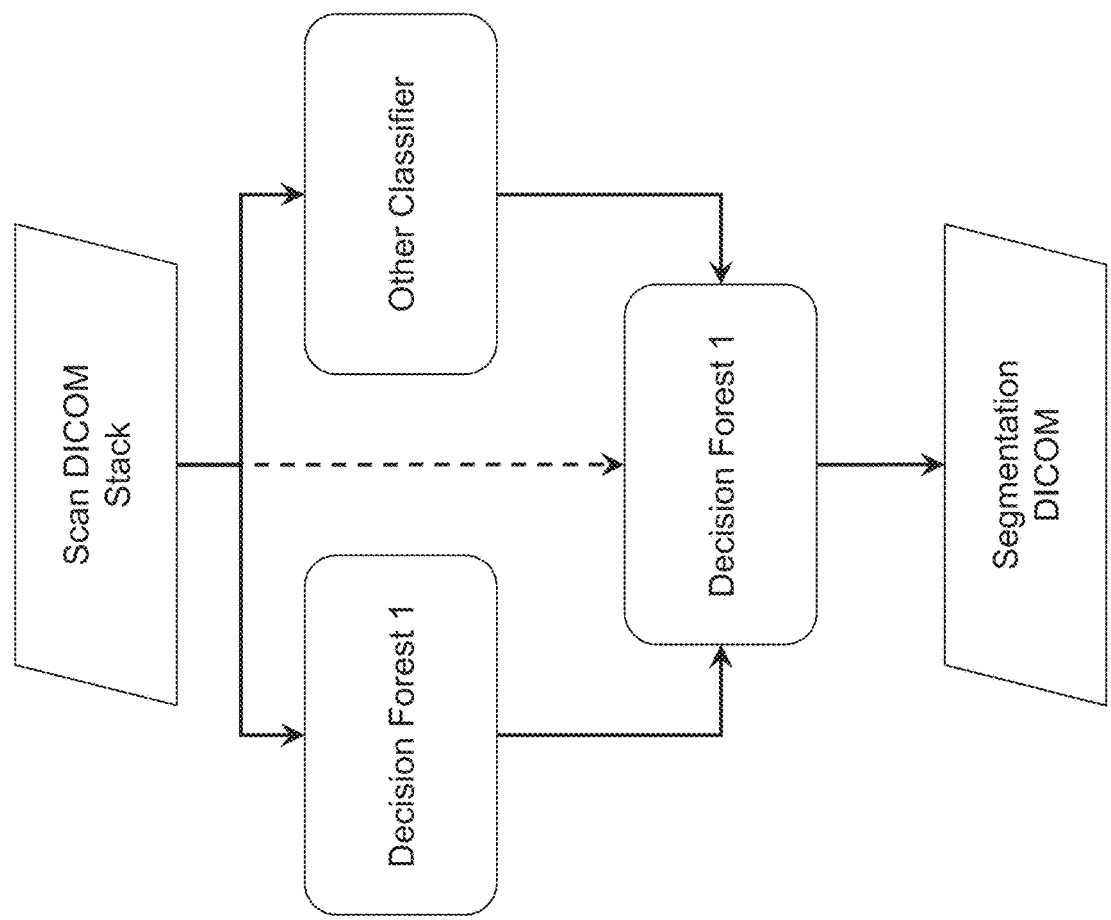
FIG. 15 is a diagram illustrating the chained decision forest workflow.

FIG. 15 is a diagram illustrating the general concept. The results from the decision tree and the results from another classifier (e. g. the threshold) are fed to a new decision tree alongside the original pixel values. In this approach, each forest-node is treated as a simple classifier that produce a score as to how likely the pixel is to being part of a bone. Each following tree will consume this estimation and make an overall assessment of the likelihood of the pixel actually being part of a bone.

2.6 Neural Network

Neural networks are similar to the Decisions Forests described above in the sense that they are built by creating very simple decision units and chaining these units together, so that what has been discovered by a few units helps a following unit to make a new estimation as to what the network is looking at.

Example of an advantage and a disadvantage of using Neural Network methods are the following:
1. Advantage: as each neuron can be trained on recognising one feature which may be either present or absent from the image, Neural Networks are extremely good at generalising common features of the subject and outperforms almost any other algorithm in the detection accuracy (including decision trees);
2. Disadvantage: although some neurons may be "looking" at a small patch of the image, any following neuron will be looking at larger and larger patches of the image; in most Neural Networks, the final neurons will be classifying very large sections if not the entire image, which may lead to very poor resolution of the boundary of the detected object.

6.1 Fully Convolutional Neural Networks: FCNN

In a typical Neural Network, the final layer will produce estimations of the input pixel belonging to a given class; in the most common approach, the neural network will take a full image of a fixed size as input and classify the entire image as to belonging to a given class. This effectively means that in the standard approach, a neural network does not produce a segmentation of the image, but a classification of the entire image; this is a little like answering the question what object is in the image, not where the object is.

An approach to solve this issue is to use a specific layout of neural network called a Fully Convolutional Neural Net. In this approach, all layers of the network are convolutional, including the final layer. Using this approach allows the system to minimise the down-scaling of the network using max pooling.

The final output of a FCNN is typically a segmentation array with a reduced resolution (a reduction of 16*16 is typical for this kind of application when using 4 2*2 max pooling layers). Just as for the decision trees discussed above, this method is expected to produce very consistent results, however a method for dealing the downscaled resolution is necessary.

2.6.2 UNETs

One of the key goals of a UNET neural network is to upscale the results of a typical neural net to the original size of the image and obtain accurate boundaries of the detected object. This is done by adding a number of up-scaling layers where the outputs of previous layers are used to identify the regions of the image and lead to a specific classification. Due to their reliance on generalised features, neural network and UNETs in particular are used at Axial3D in order to generate print ready models of CT bone tissue, bone type classification (trabecular, cortical, etc) as well as MRI scans segmentation.

3. Anatomical Feature Identification 3.1 Axial3D ATLAS

In order to facilitate the image segmentation of medical scans and to perform further classification of the detected objects, an existing knowledge of the anatomical features that may be present and their appearance within a diagnostic scan (CT, MRI, etc) must be available.

Axial3D uses a graph database in order to store such information in an ATLAS of human anatomy relevant to medical scanning techniques. In such a system, each anatomical feature is represented as a node and relationship between anatomical components are represented as relationships. Both nodes and relationships between them can be of any kind such as simple proximity, attachment, ligament, functional, etc; the nodes can represent different tissue types and organs. Both nodes and relationships contain additional information; in particular they contain a reference to a image containing such anatomical feature, its segmentation, general features of the anatomical object such as volume, surface area (if applicable), average and Standard Deviation of its Hounsfield Units.

Key features of ATLAS are:
1. to provide the Axial3D R&D and segmentation group a simple and fast information retrieval system (accessing the relevant scan and segmentation data);
2. provide a centralised area where specific information on anatomical features is stored (organ appearance and properties);
3. provide a simple method to access information of related organs;
4. provide a backbone of Ground Truth data for organ classification and automatic medical scan interpretation.

Figure 16:
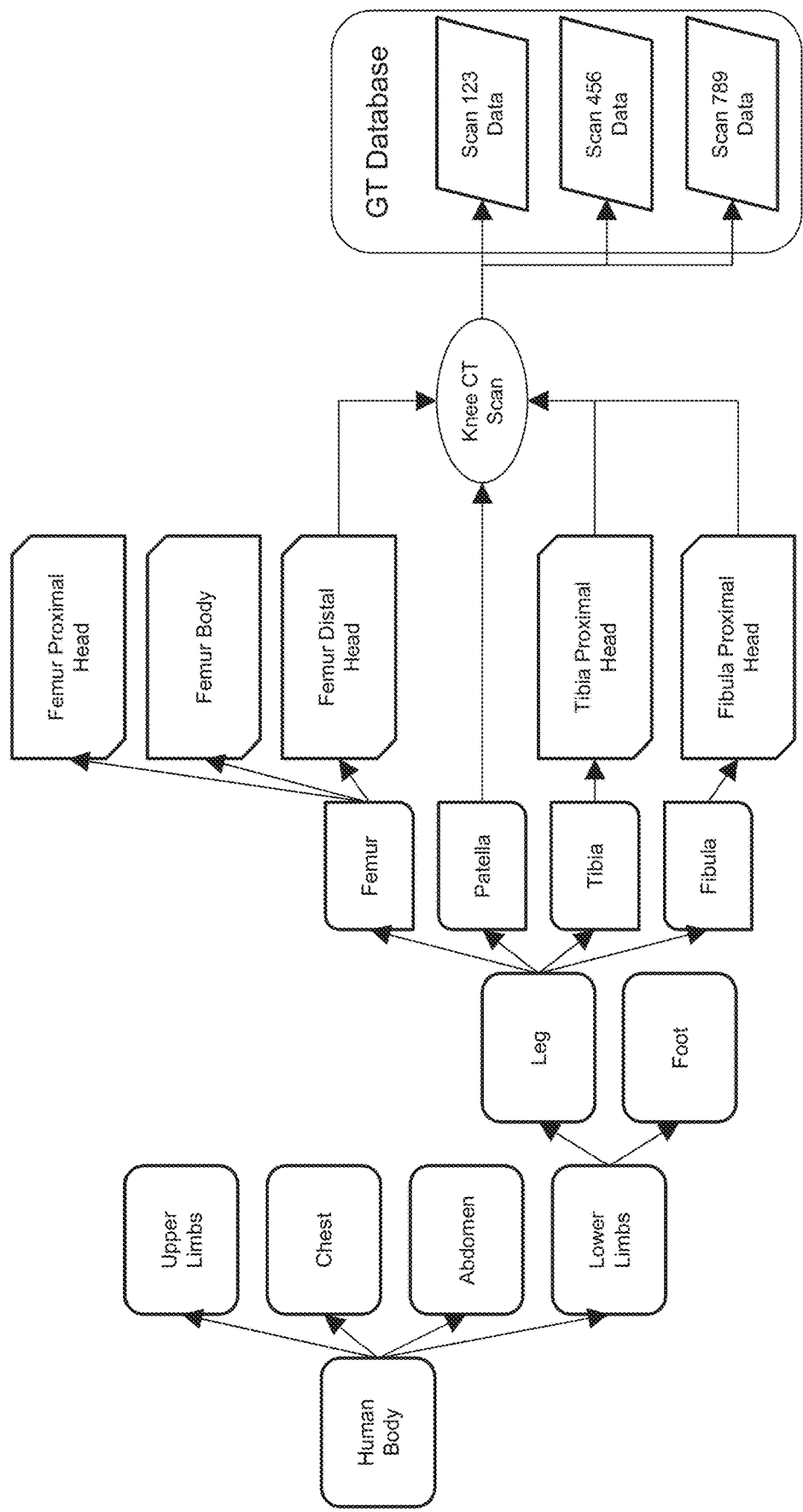
FIG. 16 is a graph database containing primary anatomical features.

Typical examples of ATLAS usage include, but are not limited to:
1. retrieve the reference of all scans in our data-store related to hips in CT scans;
2. determine the volume of all radius and ulna available in the scans;
3. determine the histogram of the Hounsfield value of lungs;
4. find all the bones typically located in close proximity to the Clavicola;

FIG. 16 shows a sample of a graph database showing the primary features to be included: the nodes represent conceptual features of the human anatomy such as regions of the skeletal system and specific bones; all the nodes are connected between each other by a belonging relationship (the ulna belong to the limb which in turns belong to the human body).

3.2 Standard Anatomical Model

A set of standard anatomical models are generated by retrieving all the available data within our data-store for a given anatomical feature in its healthy state (no pathology). The available segmentation data for a given anatomical feature (a bone, a specific organ) is registered and scaled in order to align the segmentation from the different data-sets corresponding to the various scans. The aligned and scaled segmentation data is then used to extract and compare the Hounsfield values as well as the CT scans and/or the MRI value; the similarity between each scan can then be used to generate the standard anatomical model of the feature and its expected appearance in a medical scan. Such models may also need to take into account some important aspects related to the patient from which the data comes from: for example, anatomical features are expected to vary over time as the patient ages (grow larger, some organs may become "worn out" as a result of arthritis on bones for examples, etc), sex and clinical history (some pathology will affect the appearance of the scans).

The Standard anatomical model is stored as a reference within the ATLAS and ATLAS is also available in order to facilitate the retrieval of data. As new data is added to the Axial3D database, the standard models are updated to include the new data; the history of standard model generated for each anatomical feature is also preserved.

3.3 Interesting Feature Extraction

ATLAS is used to store and retrieve data related to "interesting features" of each anatomical component. In a similar fashion as for the Standard Anatomical Model, all the segmentation related to a specific anatomical component of the human body can be retrieved and feature extraction algorithms are applied. The feature extraction algorithms take advantage of both the segmentation as well as the actual scan data in order to obtain interesting properties of the tissue or organ under consideration.

Some simple feature extraction algorithms include:
1. the anatomical component volume,
2. the component surface area,
3. its average Hounsfield unit (if CT) and standard deviation across all available scans,
4. histogram of the Hounsfield Units across all available scans,
5. Smallest bounding box that contain the anatomical component.

More complex features may include, for example:
1. key-point detection: determine the presence of keypoint landmarks; standard algorithms can be used for this purposes such as Fast, SURF, SIFT, ORB, etc; these algorithms will require adaptation in order to work with three dimensional data; the detected keypoints can be compared between the various scans and similarity between them can be preserved in the ATLAS data-store;
2. Structural and shape analysis: a number of predefined shapes and volumes can be detected within the anatomical feature being considered: for example, within the femur, the main body can be compared to a cylinder and the two heads as two spheres;

3. Anatomical Landmarks: in this approach, specific features that are unique to the specific anatomical component are detected.

The extracted interesting features are then added to the Axial3D ATLAS as part of the node properties to facilitate future reference. Axial3D is in a unique position to create such a database: due to the large volume of CT scan data as well as the availability of high quality segmentation for the scans, Axial3D can generate values that are both statistically relevant and sufficiently general to allow the creation of more advanced detection and classification algorithms (see below).

3.4 Anatomical Component Classification

The standard anatomical model and the extracted interesting features can be used in order to derive a reliable and consistent classification of the anatomical components located within the scan.

The general approach to perform such a task is the following:

1. derive accurate segmentation using the automated segmentation algorithms;
2. apply the feature extraction algorithms to the segmentation in order to derive the values of such features; note that these features may be erroneously detected if the segmentation produced poor results;
3. compare to the existing data-set of interesting features and attempt to find a number of matches;
4. the matches are constrained and filtered depending on the proximity map derived from Axial3D ATLAS;
5. the standard models are used to further refine the filtering and cross-checking by fitting a linear transform between the semi-classified segmented objects and what the standard model looks like;
6. due to the inherit inaccuracies of the segmentation step, each refinement of the matches produce a score or probability of having matched the anatomical features correctly;
7. the set of scores obtained can be used in a decision tree (or forest) in order to derive the final classification of bones;

Note that this method will not identify all anatomical features present within the scan; it will however identify a sufficient number of them to uniquely identify the region of the human body that has been scanned, its orientation, as well as the classification confidence.

3.5 Segmentation Curing, Deformities and Pathology Detection

The Anatomical classification described above provides the basis to detect any deviation from standard of a given scan:

1. Touching organ curing: It is often found that several anatomical components made up of the same tissue may be located in close proximity to each other; this is the case for example of tarsal bones, carpal bones and other joints, vessels and other cardiac tissue, etc. In some instances, the tissue that makes up the bulk of the organs are all segmented correctly, however, due to their proximity, the organs themselves are not separated correctly as individual components; in such scenarios, the touching organs will be detected as a deviation from the standard appearance of the scan and a specific algorithm for edge finding can be used to separate them as individual entities; once the segmentation curing is performed, the Anatomical Component Classification can be re-estimated and the classification confidence should have increased considerably (as more anatomical features should now be matched to the Axial3D ATLAS);

2. Implants Artefacts curing: it is quite common to obtain error in the segmentation due to the presence of foreign objects that have been implanted within the patient (pacemakers, tooth filling and braces, nails to cure scoliosis, etc); these object will appear within the scan as foreign objects with completely different properties compared to any other tissue, in particular when made of metal (titanium implants, etc); these objects will inevitably cause errors in the segmentation algorithm by introducing holes as well as misclassified organs; in a similar fashion as the touching bones algorithms described above, the implant can be identified as such with a separate tailored segmentation and classification set of algorithms; the identification of such items can then be used to correct potential errors in the organ segmentation;

3. Deformities and Pathology Detection: once the components and the scan region is identified, deviation from the normal appearance can also be used to assess the presence of some form of pathological condition and deformities; such estimation is different compared to the standard pathology detection that is performed using neural nets to classify/segment the patient data directly, it rather employs a comparative analysis of the expected appearance of an object and derives deviation from such appearance; examples of applications of such methods are the determination of skeletal deformities (flat foot, scoliosis, etc), traumatic fractures, etc.

3.6 Reconstruction Using Comparison

Figure 17:
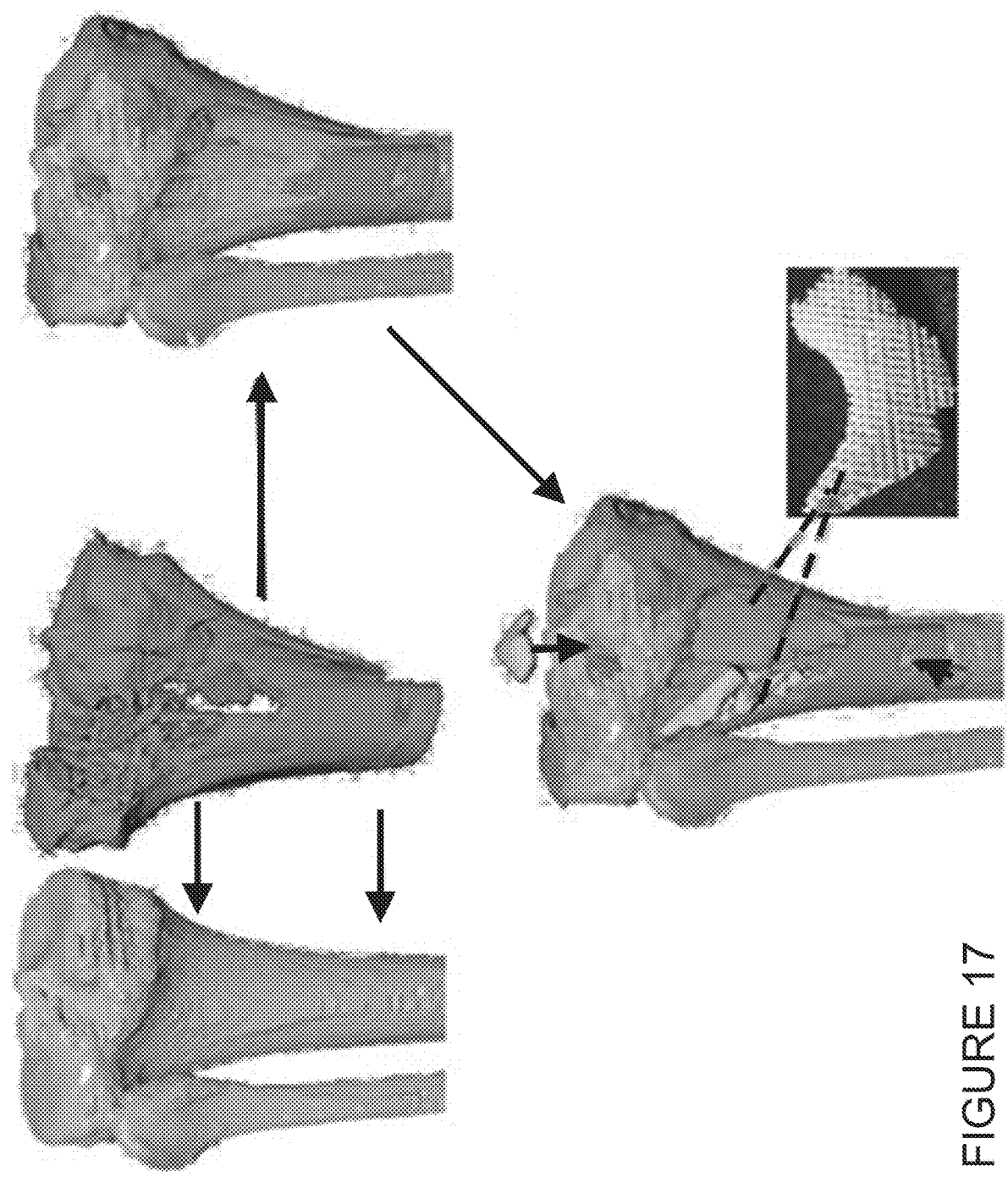
FIG. 17 are images illustrating image reconstruction using comparison.

FIG. 17 shows the results of image reconstruction using comparison. Boolean differences for bio printing can be used to assess the volume of material from a statistical model of pre-classified 'healthy' volumes of tissues and create an automatically generated 3D file of missing volume. Our automatically segmented data is assessed against statistical model of pre-segmented anatomy 'Best fit model' is created based on a statistical model for patients' anatomy to show optimal reconstruction of tissue. Missing fragments are predetermined with a best fit model and tissue scaffold models created from this.

4. 3D Model Creation

In order to obtain a 3D printable model, the segmentation data generated by applying the image segmentation algorithms, anatomical component identification and segmentation correction, a 3D surface mesh must be extracted from the scalar volumes.

For a 3D mesh to be printable, it must have the following properties:

1. all disjointed surfaces are closed manifolds (3D volumes).
2. appropriate supports are necessary to keep the disjointed surfaces/volumes in place
3. appropriate supports are necessary in order to facilitate 3D printing;
4. in order to be printable using SLA technology, all surface volumes must not be hollow (no close surfaces fully contained within other surfaces);
5. if a hollow volume is specifically requested by the clinical staff, appropriate drainage holes must be added manually by the operation team.

Once the 3D models are generated, they must be reviewed and approved by a biomedical 3D printing technician within the operations team. Whenever necessary, appropriate modifications are made by the operations team prior to printing.

4.1 Surface Extraction

For each scan, a 3D of model (surface) is created from the segmentation obtained using the methods described above. Different methods are available, including: marching cubes, marching tetrahedrons, surface nets and other isosurface methods.

A considerable amount of work has been done to compare the results of the algorithms in order to obtain the best results in terms of the following aspects:

1. anatomical accuracy: the resulting surface must be as close to the original volumetric data as possible;
2. Minimise the cuberille effect: since the iso-surface is derived from the labelled data (die segmentation) it is important to minimise the block appearance of the resulting mesh; this can be achieved by modifying the marching cube algorithm in order to force some vertices/faces to be placed on voxels that do not intersect the iso-surface directly;
3. 3D printing specific requirements: the mesh should be as close to a printable model as possible in order to facilitate the following surface conditioning steps; this means that the resulting mesh must be a manifold.

4.2 Surface Conditioning

Iso-surface extraction has a number of potential issues that need to be addressed by a conditioning stage:

1. High Poly Mesh: meshes obtained using any iso-surface extraction algorithm tend to generate models with a number of faces that is proportional to the number of voxels in the input volumetric data; meshes obtained using these approaches tend to be extremely high in their number of polygons; such a level of details is often unnecessary (a large planar surface can be represented by one single large polygon instead of several hundred small segments); poly-reduction algorithms are applied to the meshes; example of these algorithms include short edge collapse, quadratic edge decimation;
2. Mesh errors: this includes errors such as duplicated points, overlapping surfaces, missing surface; removing point-like surfaces (small unnecessary surfaces); the goal of this step is to correct some simple errors and ensure the mesh is a manifold;
3. Mesh filtering: once the meshes are reduced in poly number to an acceptable level and mesh errors are removed, simple filtering algorithms are applied in order to minimise the "pixelisation" given by the original segmentation data; the filtering radius is reduced to a minimum in order to preserve anatomical accuracy.
4. Cover holes: some organs are often only partially visible within the scan slices; in these situations the surface mesh obtained from the segmentation will not be closed; in these situations the holes are covered by additional triangles; this step must be performed after the mesh error correction and produces best results when applied after the smoothing as well; the goal of this step is to ensure all surfaces are closed manifolds.
5. Textures: The meshes are displayed to the user. We will select appropriate textures that allow the user to better visualise the anatomy. This will mean the automatic selection of different textures and lighting procedures within the display view of the application.

The expected results of this stage of mesh processing is to obtain anatomically accurate and good quality meshes that need minimal additional processing to make them "print ready". The resulting conditioned meshes are also used for displaying purposes within the web application after a further poly reduction (typically to approximately 10,000 faces).

4.3 Print Ready Models

The conditioned meshes need a further processing step in order to be printable. This step ensures that the 3D printing will successfully complete with no failures. This step includes the following modifications to the anatomically accurate models:

1. Fill in the watertight surfaces: some organs such as bones, blood vessels, stomach, etc are naturally hollow in shape resulting in a watertight hollow surface; these surfaces may fail to print when using a SLA printer due to the lack of drainage channels for the trapped resin; these organs may need to be filled prior to printing (specific requirements from the clinical staff may specify otherwise);
2. Addition of dowels to support the various organs: the 3D printed organs will require supports in order to keep their position; small dowels are added along the shortest line to join the organ together; once all possible dowels are added between all organs to be printed, a specific algorithm will remove the redundant dowels starting from the longest;
3. Addition of print supports: in most 3D printing technology the addition of small supports is required in order to facilitate the printing and achieve the best results; the supports are added by determining all local minima of the surface; the print supports are removed during printing post processing.

5. Post-Processing of 3D Printed Models

Post-Processing techniques—clear contrast in sterolithography models.

Models are created based on solid exterior X of a model and a number of internal points of interest Yn. A boolean difference is completed on X by removing Yn from its internal structure automatically. A hollow cylinder of for example 3 mm diameter is created from the surface of X to the surface of Yn with the shortest distance taken.

Pre-cut model construction—Models that are outside the bounding box of the available print volume of the printer being used will be analysed and the bounding box—5% of total model volume will be taken and a cut on the ZY plane will be automatically created. Both models will have 4×3×3 mm cylinder holes inserted in the largest surface area of the cut face. 4×2.8 mm×2.8 mm cylinders will also be created and added to the print file.

Model created in situ for bone placement analysis—bones within the scene with pre-segmented anatomy will be assessed and articular surfaces will be detected and cylinders will be inserted between two central points of articulation. Diameter of cylinder will be determined on 50% of articular surface cross sectional area.

6. Denture-Store

The methods and systems described above can also be applied to generate 3D printed physical models for dental and orthodontic labs.

In typical traditional orthodontists' practices, impressions are made and stored for up to 5 years (patient records). In busy practices, this ends up being a huge amount of physical impressions having to be stored.

Dental impressions from across the years can be 3D scanned (using available 3D scanners or with an IR laser and a turntable) and catalogued on the site.

A white light oral scanner may be purchased and all impressions may be electronically done, stored and sorted in a program.

All impressions, legacy or new, can be sent to the Axial3D system in order to generate a 3D printed physical model. The printing of the 3D physical model can also be directly completed within the dental or orthodontic lab. So all that is required is a computer and a printer to store patient data within each lab.

7. Phantom Production

Phantoms may be created for use in X-ray and CT/MRI calibration.

Different 3D printer filaments, resin or liquid have been developed

A material that will not absorb the solute containing a radioactive isotope is also developed; i.e. the model can be washed with water after use and be non-radioactive.

8. Axial3D Training:

Modular system that allows surgeons to train on various surgical procedures without the requirements for cadaver models. A pre-segmented volumetric representation of a human is displayed, using for example augmented reality (derived from both CT & MRI data) and a surgeon is able to swap out healthy tissues with the ones from Axial3D's database of rare pathologies in either virtual or physical 3D printed format. Haptic feedback is incorporated into the application to mimic different tissues when carrying out procedures.

APPENDIX: CONCEPTS SUMMARY

This section summarises the most important high-level features described above; an implementation of the invention may include one or more of these high-level features, or one or more of the key subsidiary features, or any combination of any of these.

Concept A: Entire Workflow for Generating 3D Printed Model of a Patient Specific Anatomic Feature from 2D Medical Images—Performed Automatically A method for generating a 3D physical model of a patient specific anatomic feature from 2D medical images, in which:
(a) the 2D medical images are uploaded by an end-user via a Web Application and sent to a server;
(b) the server processes the 2D medical images and automatically generates a 3D printable model of a patient specific anatomic feature from the 2D medical images using a segmentation technique; and
(c) the 3D printable model is 3D printed as a 3D physical model such that it represents a 1:1 scale of the patient specific anatomic feature.

The method may further include the following optional steps:
(a) Clinical staff can upload the 2D medical images and any additional information to the Axial3D servers using the Axial3D online web application;
(b) Clinical staff can add annotation and patient specific prescription through the Axial3D web application in order to personalise the final 3D printed product and obtain the desired results;
(c) Clinical staff can interact with any aspect of the automated 3D model generation in order to improve the final models, personalise the results and flag occasionals problems with the models prior to production and shipping;
(d) the Axial3D automated 3D model generation is a fully automated system that converts the 2D images into a final 3D printable model; the users can in real time review, annotate and modify such models through the web application prior to production and shipping;
(e) 3D model of the anatomical feature of interest (skeletal structure or joint, organ, specific tissue, etc) created by the automated system and approved by the customer is 3D printed in a 1:1 scale;
(f) The Axial3D web application employs the Axial3D fully automatic image segmentation and anatomical recognition pipeline in order to achieve near real-time display of the 3D models and allow seamless and near instantaneous update of the 3D models based on the customer feedback;
(g) All communication and the transferral of data through the network and the web application is anonymized, secured using encryption and takes advantage of Blockchain in order to orchestrate the workflow, minimise the risk of loss of data, increase transparency and minimise the time required to deliver the final 3D model;

Optional features (each of which can be combined with others) include the following:
2D medical images are uploaded alongside metadata.
metadata includes: patient's prescriptive information, medical professional information, patient information;
2D medical images are anonymised prior to being sent to a server;
the patient specific anatomic feature is automatically identified from an analysis of the 2D medical images using an anatomical knowledge dataset; machine learning is used to improve this dataset.
the patient specific anatomic feature is automatically identified from an analysis of the metadata.
analysis of the metadata is done using Natural Language Processing (NLP).
2D medical images are anonymised such that no identifiable healthcare information is being transferred;
a cryptographic hash of the patient information is created;
the system uses digital signatures to verify identity and approve decisions
a smart contract object required to order or initiate the generation of the 3D model
contains information about the requirements of the prints such as: stage quality gates,
insurance status, payment status/limits, clinician, patient consent, annotations, data
sharing agreements and/or data processing agreements;
the smart contract object is incorporated into a Blockchain;
the smart contract object is pre-agreed between the patient and the end-user;
printing of the 3D model is only executed once the smart contract object has been
validated;
dynamic pricing is generated when the smart contract object is validated; an instant quotation is displayed;
Digital currency is linked to the printing of the 3D model;
material used for printing is automatically selected depending on the specific anatomic feature;
texture used for printed is automatically selected depending on the specific anatomic feature;
when the specific anonymised feature cannot be printed by a single printer, custom 3D models are constructed, printed and combined into a single [oversized] 3D printed model.
end-user can upload data about the model being generated and annotate the model as it progresses through the workflow;

end-user can select the specific anatomy they wish to 3D print.

the uploading of the 2D medical images and the ordering process is intuitive (nontechnical person can order a 3D model);

an audit trail of the printing process is continuously updated and tracked (authorization, etc);

anomalies of the 2D medical images are detected, such as: incorrect classification of medical images, incorrect patient data, presence of foreign objects in medical images, low quality imaging data;

images which contains unwanted artefacts or background noise, such as foreign objects or a bed, are still processed;

2D medical images (CT/MRI/PET etc) can be processed together;

a preview of the specific anatomy 3D model is displayed to the end-user before the order is completed;

real time information on specific timeframe before a print is ready is generated (taking into consideration the segmentation, surface conditioning and printing);

print scheduling/distributed printing is based on inbound models and surgical requirement;

the 3D printed model is optimized based on the following patient specific parameters: scan type, bone type, tissue type, age, gender, weight;

patient specific parameters are extracted from the uploaded data;

[Hardlinking] original order and input data is applied to the physical object—QR code, NFC chip, RFID tag are added to the printed model;

Profile of end-users are saved with their preferences for particular model types; segmentation of the 2D medical images is performed to classify each pixel within the medical images;

segmentation technique that is used is one of the following: threshold, decision tree, chained decision forest or neural network method;

segmentation technique that is used is a combination of the following techniques: threshold, decision tree, chained decision forest or neural network method.

segmentation is done by applying a threshold to generate a set of 2D threshold images representing a patient specific anatomic feature;

the segmentation step is combined with an anatomic feature identification algorithm;

a 3D surface mesh model is generated for each set of 2D threshold images;

the threshold value is generated from the 2D medical images histogram analysis;

the threshold value is generated from detecting the peaks of histogram corresponding to tissues similar to the tissue of the patient specific anatomic feature.

the threshold value is a function of the type of 2D medical images (CT, MRI, PET or SPCET);

the threshold value is a function of the CT scanning parameters (X-Ray energy and flux);

the threshold value is a function of the bone type (hard or soft);

the end user selects the scan type or bone type;

the threshold value is not selected by an end-user.

the 3D surface mesh models are compressed, smoothed and reduced before sending them bach to the end-user device;

the generation of the 3D model is performed by parallel processing; end-user is alerted when an anomaly is detected;

one or more threshold values are used in order to generate one or more 3D surface mesh model;

the end-user selects one of the one or more 3D surface mesh models he wishes to print;

Concept B: UX—Real Time User Interaction

Computer implemented method comprising the steps of: receiving from an end-user a set of 2D medical images specific to a patient, automatically segmenting the set of 2D medical images and creating a 3D printable model from the set of 2D segmented medical images, and displaying the 3D model to the end-user.

The computer implemented method may further comprise the optional following steps:

a) The user can send a set of 2D medical images specific to a patient to the Axial3D server through the web application;

b) A 3D model candidate, generated by the Axial3D image analysis pipeline identifying the anatomical components within the images, is used to generate a 3D model of the organs of interest;

c) the results of the image analysis and the 3D printable models created are displayed to the user through the Axial3D web application;

d) The web application allows the user to provide contextual information regarding the patient and the prescription;

e) The web application provides a basic level of functionality to enable the end-user to interact with, modify the results and select the 3D automatic image analysis; this includes the selection of volumes to be printed, select the materials and the anatomical fidelity level required (the model accuracy), flag for gross miscalculations and require a segmentation engineer to review the results;

f) The web application allows the user to trigger the generation of a new model based on the prescription and the annotation provided; a new model is then displayed;

g) the clinical staff (customers) can accept the model once satisfactory results are shown;

h) Using this semi-automatic approach allows extremely accurate and high fidelity 3D printable models to be obtained within a few minutes instead of the several hours it would otherwise require;

i) the users can select to skip any of the steps described above.

Optional features (each of which can be combined with others) include the following:

this semi-automatic system relies on the ability to perform image analysis and anatomical recognition to an exceptional degree of accuracy within very short timescales (seconds) based on the user feedback; such feedback can be expressed either as free text or as actions performed on the 3D models; the task of performing the image analysis is devolved to the Axial3D medical image segmentation and recognition (see Concept C).

The data is sensitive in nature and covered by privacy law; all data transmitted across the network is anonymized, encrypted and compressed prior to transmission; the integrity of all exchanged data is verified through data checksum;

all data exchanged within one single order is covered by a Blockchain virtual contract; the virtual contract is created prior to the 2D scan image data is transmitted to the Axial3D servers, such scan data alongside all segmentation and 3D model data is also covered by the same virtual contract; acceptance of the final model will trigger the completion of the virtual contract;

end-user can easily annotate the anatomic feature;

end-user can select anatomic feature they wish to 3D print;

3D model is 3D printed to represent a 1:1 scale of the specific anatomic feature;

threshold values are generated from the medical images histogram analysis;

threshold values are function of the type of 2D medical images (CT, MRI, PET or SPCET);

threshold values are function of the CT scanning parameters (X-Ray energy and flux);

threshold values are function of the bone type (hard or soft);

the end user selects the scan type or bone type;

the threshold value is generated from the 2D medical images histogram analysis;

the threshold value is generated from detecting the peaks of histogram corresponding to tissues similar to the tissue of the patient specific anatomic feature.

the set of 2D medical images is anonymised before being sent to a server;

tine server sends back the 3D surface mesh models back to the end-user device;

the 3D surface mesh models are compressed, smoothed and reduced before sending them back to the end-user device;

the generation of the 3D model is performed by parallel processing;

end-user is alerted when an anomaly is detected;

end-user can upload data about the model being created and annotate the model;

instant quotation is displayed.

Concept C: Image Processing Method for Converting 2D DICOM Image Series into a 3D Printable Model.

Computer implemented method for automatically converting 2D DICOM image series into a 3D printable model in which the method includes an automatic segmentation step.

Optional features (each of which can be combined with others) include the following:

1. Anatomical Tissue Segmentation: obtain accurate and high fidelity detection of the tissue of interest;
   a. tissues that are identified are: osseous tissue; fatty tissue (including liver), epithelial tissue (glands, kidneys, pancreas); squamous epitelial tissues (skin); cardiac tissue; tubular tissue (veins, lymphatic vessels); lungs; cerebral tissue (brain, primarily from MRI);
   b. The segmentation is performed using multiple segmentation algorithms (3 thresholds values, Decision Trees, Neural Nets) and combines their results into one final segmentation that is both high fidelity and accurate (the NN is covered by Concept D);
2. Anatomical Recognition (Concept E): the tissues are grouped into organs and a full picture of the body parts is derived (E.G spleen, liver, part of the lungs and few ribs may be recognised together within the same scan); the grouping is performed by a classifying neural network; this NN contains a small number of convolutional layers and is followed by a fully connected section;
3. Segmentation Correction: once the anatomical organs and features are correctly identified, minor errors in the results of the tissue segmentations can be corrected; errors include primarily separation of tissues in close proximity (joined bones) and small miss-detected regions;
4. Foreign Bodies Identification (Concept E): implants (orthopedic metal implants, dental implants and fillings, etc), pacemakers, unknown foreign bodies (swallowed objects);
5. Selection of the organs/anatomical features: these are the features that will eventually be printed; the anatomical features of interest are derived primarily from the prescription provided by the clinicians;
6. Print Ready Model Generation: the segmented and identified volumes are converted into a print ready model:
   a. The 3D surface for the anatomical features of interest is generated;
   b. die 3D surface undergoes simple mesh cleaning algoridims in order to render it printable (decimation, ensure manifold structures, fill holes within the mesh)
   c. each volume is assigned a material
   d. die 3D printing technology is selected
   e. Dowels and support are added Both the training of classifiers and the recognition algorithms take advantage of the Axial3D database (Concept F) of pre-labelled scans (Ground Truth); the Axial3D database contains the GT itself as well as a Graph Database describing an Ontology of anatomical features; the ontology is tailored taking into account 3D medical imaging practices within the radiology and standard 3D medical imaging techniques (see following concept)

Concept D: Specific Neural Network Processing

Computer implemented method for generating a 3D printable model of a patient specific anatomic feature from the patient 2D medical images in which the method includes the step of segmenting the patient 2D medical images using a neural network trained from a database of existing medical images.

Optional features (each of which can be combined with others) include the following:

the segmentation step is performed automatically;

the method is capable of handling several scanning modalities: in particular CT, MRI and/or PET scans are supported;

A variety of tissues are supported: these include osseous tissue; fatty tissue (including liver), epithelial tissue (glands, kidneys, pancreas); squamous epitelial tissues (skin); cardiac tissue; tubular tissue (veins, lymphatic vessels); lungs; cerebral tissue (brain, primarily from MRI)

the neural network includes only convolutional, downsampling and upsampling layers; the neural network design does not include any fully connected layer; the technology combines the ideas of uNET and FCNN in order to obtain the best segmentation in terms of anatomical fidelity in regards to the edge of the anatomical components;

the results of the neural network segmentation are combined with the results of other segmentation techniques such as: threshold-based, decision tree, chained decision forest method; This is done in order to maximise the anatomical fidelity;

The training of the Neural Network is performed by using the Axial3D Scan Database containing labelled data (the Ground Truth) and the medical imaging ontology (Concept E).

Concept E: Anatomical Feature Identification

Computer implemented method for identifying an anatomic feature from a medical image, the method includes:
(a) classifying each pixel with the medical image by using a segmentation method;
(b) establishing links between the different pixels from the exploration of a graph database, wherein the graph database stores information on human anatomy relevant to medical image scans; and
(c) identifying the anatomic feature from the previously established links.

Optional features (each of which can be combined with others) include the following:
segmentation method is automatic
method provides a score or probability that the anatomic feature has been correctly identified.

The method is optionally, further configured to:
retrieve the reference of all scans in our data-store related to hips in CT scans;
determine the volume of all radius and ulna available in the scans;
determine the histogram of the Hounsfield value of lungs;
detect and identify the bones located in close proximity of the Clavicola;
determine the state of the anatomic feature such as healthy, or pathology;
identify the type of anatomic feature such as tissue type or organ type.
extract additional information such as: HU standard deviation or average value, estimated
anatomic feature volume, estimated anatomic feature surface area;
update the graph database.

Concept F: 3D Medical Imaging DB

Computer implemented method for creating a graph database of medical images anatomic features, the method comprising the following steps:
a) Store medical images from CT, MRI, PET scans;
b) Store the labels (Ground Truth) for the scan;
c) Populate a graph database based on standard medical ontologies tailored to 3D medical imaging application; the ontology is represented as a series of nodes connected with each other through functions, proximity and anatomical groupings and the frequency of appearing in the same 2D medical image;
d) Holds links between the ontologies and GT datasets (both the scan and the label data).

The GT database contains the 2D scan images alongside the labels; each scan and relative labels data is approved by the biomedical engineers prior to the insertion into the database; each set of scan and relative labels are derived from:
Manually labelled data, labelled either by clinical staff and made available through an open database or by the Axial3D team of biomedical engineers;
Data derived from the automated segmentation pipeline that has been reviewed and corrected by a biomedical engineer or clinical staff,
Data derived from manually labelled data to which synthetic transformations have been applied (synthetic GT);

The Axial3D Medical Imaging DB is used to perform the following tasks:
1. retrieve all scans showing a specific anatomical feature;
2. create generalized models of anatomical features based on the existing data;
3. generate the training and testing sets when training image classifiers algorithms;
4. support the anatomical entity identifications once a rough segmentation is performed.

Optional features (each of which can be combined with others) include the following:
medical images are 2D medical scans such as CT, MRI and/or PET scans;
a node contains a reference to a medical image with the corresponding anatomic feature;
a node contains a reference to the results of the segmentation of a medical image with the corresponding anatomic feature;
a node also holds informations relating to the anatomic feature such as volume, surface area, Hounsfield Unit standard deviation or average.
additional metadata associated with the medical image are also received alongside the medical images;
metadata includes: patient's prescriptive information, medical professional information, patient information.

Concept G: Design of Objects for Bioprinting—Including Creation of Idealised Version of Anatomical Features A method for generating 3D models of portions of anatomy based on anatomical database or mirroring for use in replacing pathological tissues in the body.

Optional features (each of which can be combined with others) include the following:
(a) identification and classification of anatomy from 2D medical images; leveraging a knowledge base of healthy tissues and a connectivity map of the adjacent tissue. This can be used to classify abnormal anatomy as a deviation from the norm. The use of a generalised knowledge base of the 3D shapes of anatomy and their connectivity to identify non-normal features of anatomy.
(b) the generation of idealized 3D models of patient anatomy based on a database of known healthy tissues, organs and anatomical features; the idealised model is patient specific and involves a number of parameters including age, gender, weight and height as well as the identification of the analogous mirrored healthy organ if available;
(c) a method to register and spatially align the 3D models of pieces of anatomy. This method can be used to identify differences between the defective and the idealized models in order to derive the defective portion;
(d) a method to derive the defective portion; this method will be sufficiently robust so that small differences between the 3D models such as noise and the inherent variability of the human anatomy are not included in the final defective portion (edges);
(e) a method for generating the structure of the 3D printable lattice for final 3D bio-printing; the lattice type and structure (regular or irregular) and parameters (cell size, density) will be tissue & patient specific to the portion of anatomy in question that will be replaced;
(f) a method to manually review and approve the final defective portion against idealised anatomy and prepare the model for final 3D bio-printing.

Note

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred example(s) of the invention, it will be apparent to those of ordinary skill in the art that numerous modifications can be made without departing from the principles and concepts of the invention as set forth herein.

What is claimed:

1. A computer-implemented method for defining patient specific anatomical features from medical images, the computer-implemented method comprising:
receiving medical images and information on bone and/or soft tissue of a patient;
applying the information as an input to a segmentation algorithm to automatically process the medical images to assign a label for each pixel of the medical images based at least partially on the bone and/or soft tissue, the segmentation algorithm including a convolutional Neural Network method trained from a database of existing medical images that have been labelled and a medical imaging ontology;
accessing a database of medical image anatomical features;
using an anatomical feature identification algorithm to probabilistically match the labeled pixels of the medical images against the database of medical image anatomical features to generate segmentation data that defines one or more patient specific anatomical features based on the labeled pixels of the medical images; and
generating a 3D model of the one or more patient specific anatomical features comprising the bone and/or soft tissue using the generated segmentation data.

2. The computer-implemented method of claim 1, wherein the information on bone and/or soft tissue of the patient comprises information of a type of the bone and/or soft tissue within the medical images.

3. The computer-implemented method of claim 2, wherein the information of the type of bone and/or soft tissue is inputted by a user.

4. The computer-implemented method of claim 2, wherein the information of the type of bone and/or soft tissue is captured from the medical images.

5. The computer-implemented method of claim 1, wherein the segmentation algorithm comprises at least one of the following multiple segmentation techniques: threshold-based, decision tree, chained decision forest, or neural network method.

6. The computer-implemented method of claim 5, further comprising combining results of each of the multiple segmentation techniques together to derive a final segmentation result.

7. The computer-implemented method of claim 5, wherein the segmentation algorithm includes a thresholding algorithm that automatically estimates a threshold value for a pixel being classified as bone or soft tissue, the threshold value optimized based on one or more of the following parameters: scan type, bone type, tissue type, age, gender, and weight of the patient.

8. The computer-implemented method of claim 7, wherein the threshold value is estimated from a histogram analysis of the medical images.

9. The computer-implemented method of claim 8, wherein the histogram analysis comprises detecting peaks of a 2D medical images histogram corresponding to bone and/or soft tissue similar to bone and/or soft tissue within the medical images and, for each detected peak of the 2D medical images histogram:
deriving or determining a detected peak inflection point by calculating a zero of a 2D medical images histogram second derivative in proximity of a peak; and
deriving or determining an inflection offset between the peak and the inflection point,
wherein the estimated threshold value corresponds to the position of the detected peak with an offset corresponding to three times the derived or determined inflection offset.

10. The computer-implemented method of claim 9, wherein, if an error occurs during peak detection of the 2D medical images histogram, the thresholding algorithm applies a default threshold value based on at least one of the bone and/or soft tissue of the patient or a scan type of the medical images.

11. The computer-implemented method of claim 7, wherein the segmentation algorithm includes the thresholding algorithm in combination with a smoothing algorithm, the smoothing algorithm comprising a Gaussian filter.

12. The computer-implemented method of claim 11, wherein the thresholding algorithm uses a logistic probabilistic function to calculate a likelihood of a pixel being a bone or soft tissue in question.

13. The computer-implemented method of claim 7, wherein the thresholding algorithm is configured to segment out bone from background information within the medical images.

14. The computer-implemented method of claim 7, wherein the bone type is selected from a list consisting of hard bone and soft bone.

15. The computer-implemented method of claim 7, wherein the scan type is selected from a list consisting of CT, MRI, PET and SPECT.

16. The computer-implemented method of claim 7, wherein the scan type is inputted by a user.

17. The computer-implemented method of claim 7, wherein the segmentation algorithm includes a chained decision forest, in which a hierarchy of decision forests is used, wherein results of a decision tree and results from the thresholding algorithm are fed to a new decision tree alongside pixel values of the medical images.

18. The computer-implemented method of claim 17, wherein each forest-node of the chained decision forest is treated as a simple classifier that produces a score indicative of a likelihood of a pixel being a bone or soft tissue in question.

19. The computer-implemented method of claim 17, wherein the decision tree is created based on one or more of the following properties of medical images pixels: number of pixels resembling bone or soft tissue of interest located near a pixel in question, number of pixels resembling bone or soft tissue of interest located near a given pixel, or overall gradient of the image at a given pixel.

20. The computer-implemented method of claim 17, wherein the decision tree is applied to a subset of pixels within the medical images and labels obtained from the subset are then up scaled using standard interpolation methods to recover segmentation of the full image and, wherein the subset of pixels is generated by subsampling the medical images, and wherein a subsampling stride is selected depending on pixel size.

21. The computer-implemented method of claim 1, wherein the convolutional Neural Network method comprises at least one of a Fully Convolutional Neural Network (FCNN) or a UNET Neural network.

22. The computer-implemented method of claim 1, wherein the database of medical image anatomical features comprises a graph database comprising nodes representing anatomic features including tissue type or organ type, and edges associated with relationships between the nodes, including: has part, proximity, attachment, ligament, or functional, wherein a node includes: a reference to a medical image with a corresponding anatomic feature, a reference to results of segmentation of a medical image with a corresponding anatomic feature, information relating to the anatomic feature including volume, surface area, or Hounsfield Unit standard deviation or average, and wherein the graph database is updated after the generation of a 3D model.

23. The computer-implemented method of claim 1, further comprising:
    detecting touching bones or soft tissues within the 2D medical images; and
    using an edge finding algorithm to separate different bones or soft tissues.

24. The computer-implemented method of claim 1, further comprising detecting a pathology of the one or more patient specific anatomical features comprising the bone and/or soft tissue by measuring deviation of the 3D model from an expected appearance of the one or more patient specific anatomical features comprising the bone and/or soft tissue.

25. The computer-implemented method of claim 24, wherein the pathology of the one or more patient specific anatomical features comprising the bone and/or soft tissue comprises a skeletal deformity.

26. The computer-implemented method of claim 1, wherein the medical images are MRI images.

27. A system for defining patient specific anatomical features from medical images, the system comprising at least one processor configured to:
    receive medical images and information on bone and/or soft tissue of a patient;
    apply the information as an input to a segmentation algorithm to automatically process the medical images to assign a label for each pixel of the medical images based at least partially on the bone and/or soft tissue, the segmentation algorithm including a convolutional Neural Network method trained from a database of existing medical images that have been labelled and a medical imaging ontology;
    access a database of medical image anatomical features;
    use an anatomical feature identification algorithm to probabilistically match the labeled pixels of the medical images against the database of medical image anatomical features to generate segmentation data that defines one or more patient specific anatomical features based on the labeled pixels of the medical images; and
    generate a 3D model of the one or more patient specific anatomical features comprising the bone and/or soft tissue using the generated segmentation data.

28. The system of claim 27, wherein the information on bone and/or soft tissue of the patient comprises information of a type of the bone and/or soft tissue within the medical images.

29. The system of claim 27, wherein the segmentation algorithm comprises at least one of the following multiple segmentation techniques: threshold-based, decision tree, chained decision forest, or neural network method.

30. The system of claim 29, wherein the segmentation algorithm includes a thresholding algorithm that automatically estimates a threshold value for a pixel being classified as bone or soft tissue, the threshold value optimized based on one or more of the following parameters: scan type, bone type, tissue type, age, gender, and weight of the patient.

* * * * *